(12) United States Patent
McCarthy et al.

(10) Patent No.: US 7,776,022 B2
(45) Date of Patent: Aug. 17, 2010

(54) APPARATUS AND METHODS FOR MAKING, STORING, AND ADMINISTERING FREEZE-DRIED MATERIALS SUCH AS FREEZE-DRIED PLASMA

(75) Inventors: Simon J McCarthy, Portland, OR (US); John W. Morgan, Portland, OR (US); William D. Block, Lake Oswego, OR (US)

(73) Assignee: HemCon Medical Technologies, Portland, OR (US)

( * ) Notice: Subject to any disclaimer, the term of this patent is extended or adjusted under 35 U.S.C. 154(b) by 643 days.

(21) Appl. No.: 11/725,352

(22) Filed: Mar. 19, 2007

(65) Prior Publication Data

US 2008/0234652 A1 Sep. 25, 2008

(51) Int. Cl.
*A61B 19/00* (2006.01)
*A61M 5/32* (2006.01)
(52) U.S. Cl. .................. 604/408; 604/403; 604/415
(58) Field of Classification Search ............... 604/403, 604/408, 410, 415; 383/210.1; 206/363
See application file for complete search history.

(56) References Cited

U.S. PATENT DOCUMENTS

| | | | |
|---|---|---|---|
| 4,035,924 A | 7/1977 | Faure | |
| 4,878,597 A | 11/1989 | Haast | |
| 4,973,327 A | 11/1990 | Goodrich, Jr. et al. | |
| 5,084,040 A | 1/1992 | Sutter | |
| 5,114,004 A * | 5/1992 | Isono et al. ............... 206/222 |
| 5,257,983 A | 11/1993 | Garyantes et al. | |
| 5,309,649 A | 5/1994 | Bergmann | |
| 5,342,673 A | 8/1994 | Bowman et al. | |
| 5,631,019 A * | 5/1997 | Marx .................. 424/450 |
| 5,853,388 A * | 12/1998 | Semel ................... 604/82 |
| D425,205 S | 5/2000 | Henigan et al. | |
| D430,939 S | 9/2000 | Zukor et al. | |
| 6,199,297 B1 | 3/2001 | Wisniewski | |
| 6,517,526 B1 | 2/2003 | Tamari | |
| 2002/0189127 A1 | 12/2002 | Akimoto | |
| 2005/0277107 A1 | 12/2005 | Toner et al. | |
| 2007/0258960 A1 | 11/2007 | DeAngelo et al. | |
| 2008/0176209 A1 | 7/2008 | Muller et al. | |
| 2008/0177243 A1 * | 7/2008 | Roger .................. 604/410 |

FOREIGN PATENT DOCUMENTS

WO    WO2008/048228    4/2008

* cited by examiner

*Primary Examiner*—Leslie R Deak
(74) *Attorney, Agent, or Firm*—Ryan Kromholz & Manion, S.C.

(57) ABSTRACT

A freeze-dried material is stored in a first chamber of a container along with a reconstituting liquid for the freeze-dried material, which is stored in a second chamber of the container. A sealing wall within the container forms a barrier between the first chamber and the second chamber preventing contact between the freeze-dried material and the reconstituting liquid. At least one valve assembly in the sealing wall selectively opens a region of the sealing wall to establish fluid flow communication between the first and second chambers, allowing the freeze dried material to be reconstituted. The reconstituted freeze-dried material can be administered from the same container to a recipient.

9 Claims, 15 Drawing Sheets

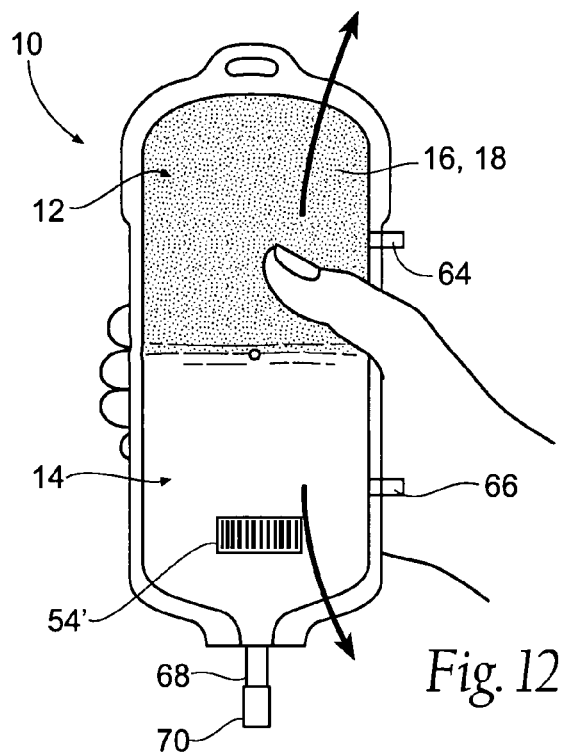
Fig. 12
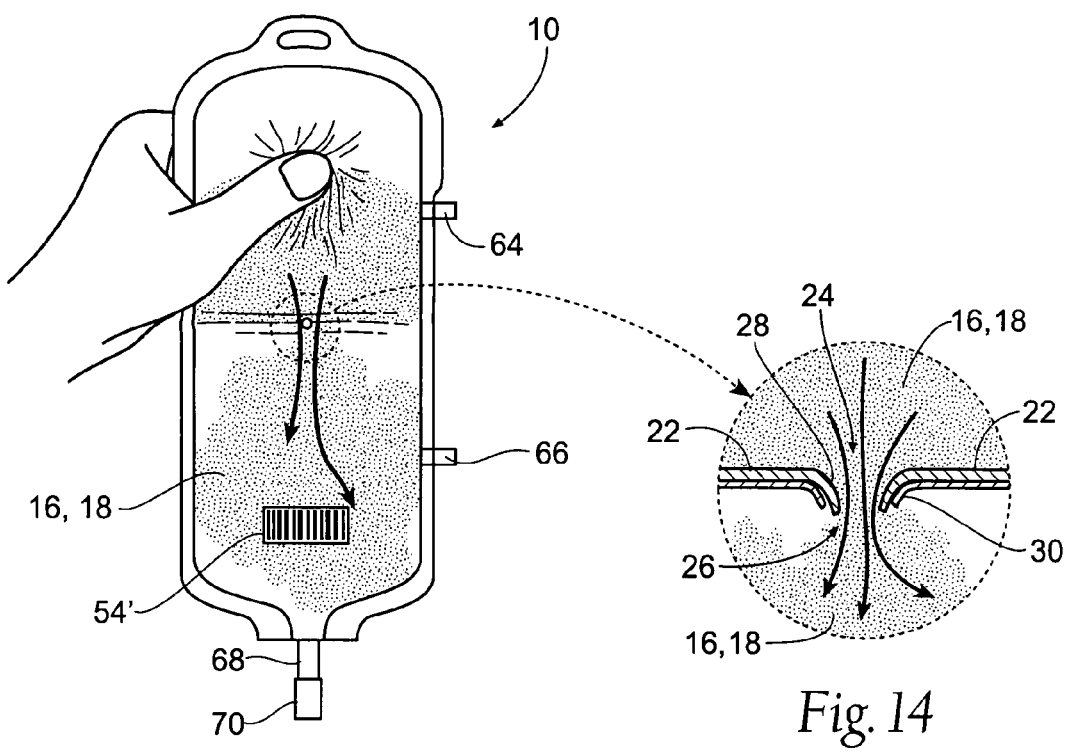
Fig. 13
Fig. 14

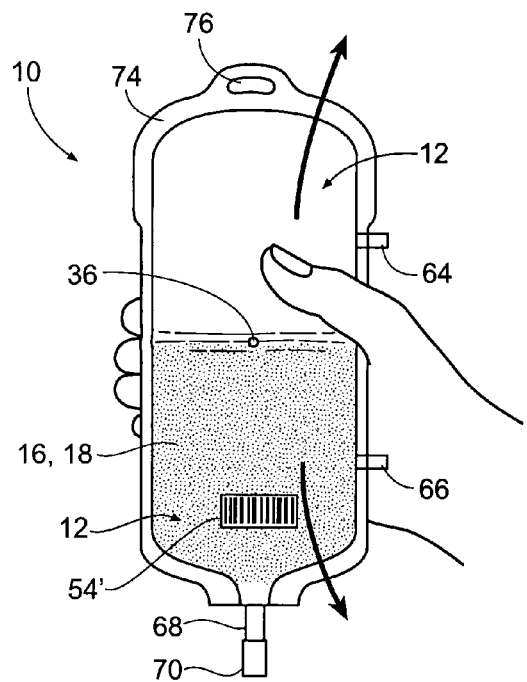
Fig. 15
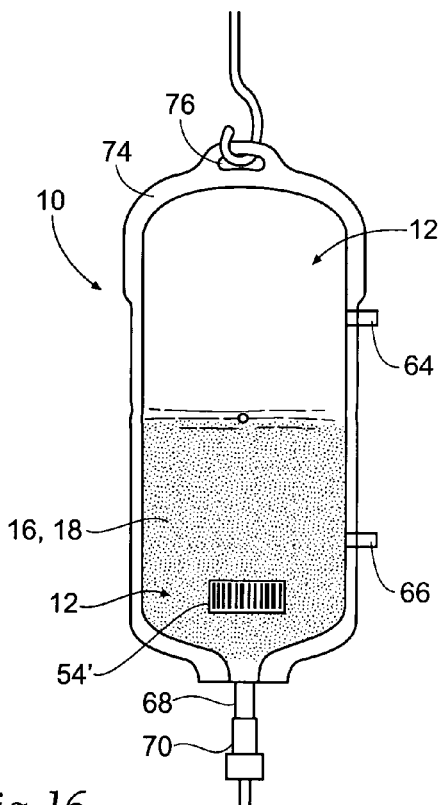
Fig. 16
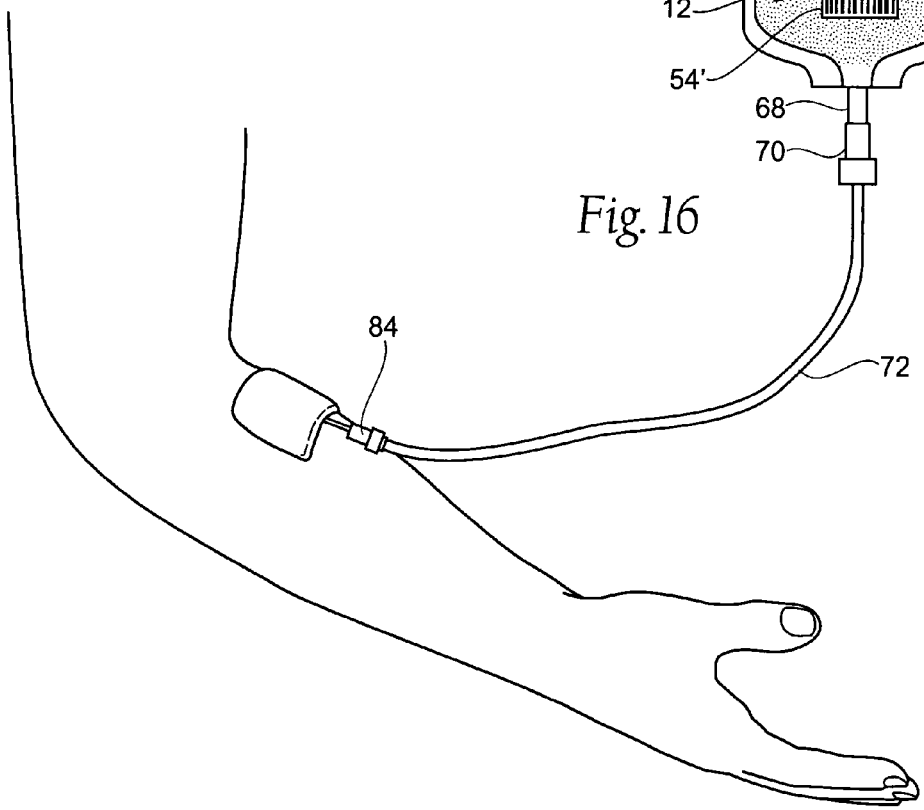

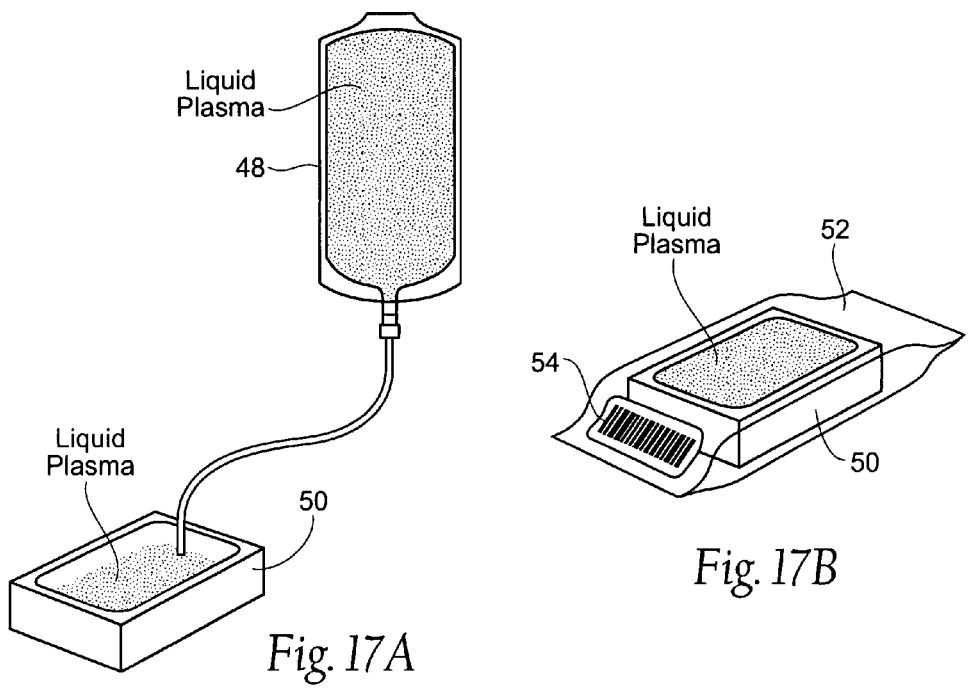
Fig. 17A
Fig. 17B
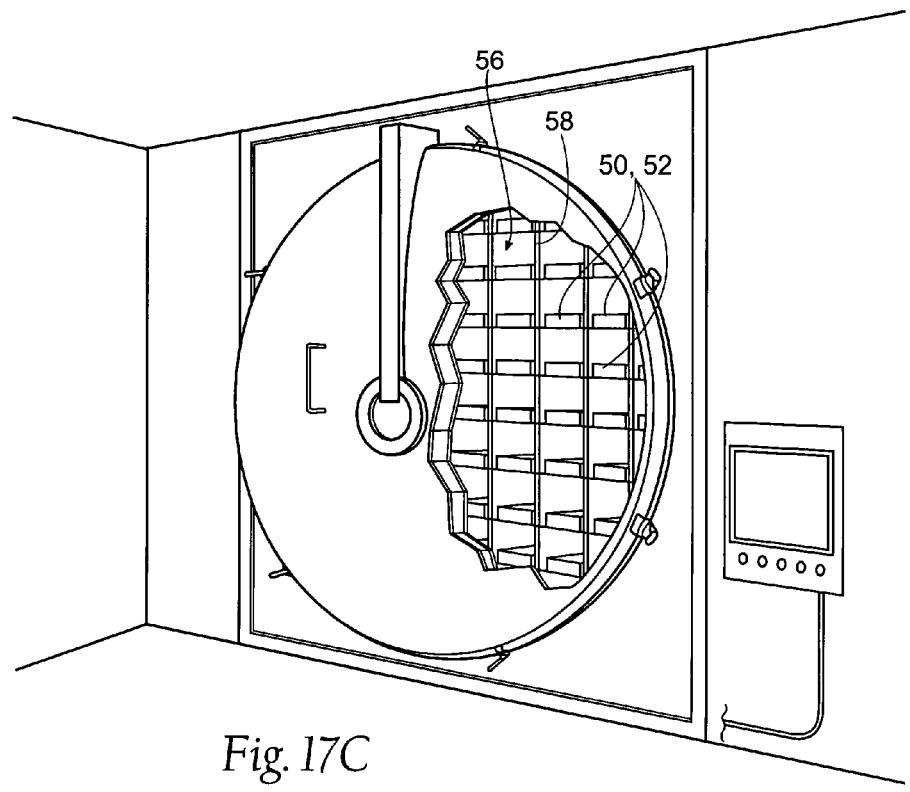
Fig. 17C

APPARATUS AND METHODS FOR MAKING, STORING, AND ADMINISTERING FREEZE-DRIED MATERIALS SUCH AS FREEZE-DRIED PLASMA

FIELD OF THE INVENTION

The present invention relates to methods, systems, and apparatuses for manufacturing, storing and administering freeze-dried materials, such as single donor units of freeze-dried human plasma.

BACKGROUND OF THE INVENTION

First aid is critical for the survival of a person that has suffered a serious injury, such as a trauma victim. For instance, initial treatment of a severely wounded person in combat situations can often mean the difference between life and death. While it is necessary to treat the wounds and stop the bleeding of the person, it is also important to ensure that the person's body is capable of properly functioning. Thus, it is necessary to take steps to ensure that the person's body is properly hydrated after losing fluids due to the injury. The present invention addresses these issues.

Previously, fluids were replenished within the patient by delivering saline intravenously. While effective, research has indicated that delivery of plasma to the patient is even more effective in replenishing fluid to the patient than the use of saline. However, delivery and storage of the plasma is critical to prevent contamination of the plasma. An ideal way of delivering the plasma is to deliver the plasma in a freeze dried form and reconstituting the plasma when it is administered to a person.

SUMMARY OF THE INVENTION

The invention provides methods, systems, and apparatuses for manufacturing, storing and administering freeze-dried materials, such as single donor units of freeze-dried human plasma.

According to one aspect of the invention, a freeze-dried material, e.g., freeze-dried human plasma, is stored in a first chamber of a container along with a reconstituting liquid for the freeze-dried material, e.g., de-gassed water. The reconstituting liquid is stored in a second chamber of the container. A sealing wall within the container forms a barrier between the first chamber and the second chamber preventing contact between the freeze-dried material and the reconstituting liquid. At least one valve assembly in the sealing wall can be manipulated to selectively open at least one region of the sealing wall to establish fluid flow communication between the first and second chambers. This allows the freeze dried material to be reconstituted within the container. The reconstituted freeze-dried material can also be administered directly from the same container to a recipient.

In one arrangement, the valve assembly includes a pressure sensitive valve, e.g., a flap valve. The valve is operative between a normally closed condition, normally resisting fluid flow communication between the first and second chambers, and an opened condition, establishing fluid flow condition communication between the first and second chambers. The pressure sensitive valve can be placed in its open condition in response to establishing a pressure differential across the valve, e.g., by preferentially squeezing a chamber of the container.

In one arrangement, the valve assembly includes a normally closed septum. The septum is operative in a normally closed condition, maintaining closure between the first and second chambers, and an opened condition establishing fluid flow communication between the first and second chambers in response to at least a partially tearing of the septum. The septum can, e.g., include a tear member coupled to a pulling member to at least partially tear open the septum.

The pressure sensitive valve and the septum can be arranged serially to provide a redundant valve assembly. In this arrangement, the normally closed septum is operative in a normally closed condition, maintaining closure between the first and second chambers, independent of the valve and an opened condition establishing fluid flow communication between the first and second chambers in response to at least a partially tearing of the septum and a pressure differential applied across the valve.

In one arrangement, an outer skirt is provided that overlays an exterior wall of the container in a region of the sealing wall. The outer skirt can include a tear member coupled to a pulling member to tear open the outer skirt for removal.

Another embodiment of the invention provides a method that provides a flexible container as above generally described, with first and second chambers. The first chamber holds a freeze-dried material, such as freeze-dried human plasma, in a dry state. The second chamber holds a reconstituting liquid for the freeze-dried material. An interior sealing wall within the container is sized and configured to form a barrier between the first chamber and the second chamber preventing contact between the freeze-dried material and the reconstituting liquid. At least one valve assembly in the sealing wall is operative by manipulation to open at least one region of the sealing wall to establish fluid flow communication between the first and second chambers. According to this aspect of the invention, the valve assembly is manipulated to open the region, and the reconstituting liquid is expressed from the second chamber through the valve assembly into the first chamber into contact with the freeze-dried material.

In one arrangement, an outer skirt overlays an exterior wall of the container in a region of the sealing wall and blocking manipulation of the valve assembly. In this arrangement, the outer skirt is removed to expose the valve assembly to manipulation prior to manipulating the valve assembly to open the region in the sealing wall.

In another arrangement, the reconstituted freeze-dried plasma is administered directly from the container to a recipient.

According to another aspect of the invention, a freeze-dried material comprising freeze-dried human plasma is prepared and stored, transported, reconstituted, and administered using a container as just generally described in any of the foregoing paragraphs. In one arrangement, liquid human plasma is loaded in molds. The molds are cooled until they reach approximately −45° C. The plasma is dried so the moisture content is below 5% w/w, thereby forming the freeze-dried human material that can be stored, transported, reconstituted, and administered using a container.

These and other areas of importance and significance will become apparent from following description.

BRIEF DESCRIPTION OF THE DRAWINGS

FIGS. 10 to 15 are front elevation view of the device shown in FIG. 9, showing the manipulating the device to reconstitute the freeze-dried materials.

FIG. 16 is a front elevation view of the device shown in FIG. 15, showing the administration of reconstituted material directly from the device to a recipient.

FIGS. 17A to 17E are diagrammatic perspective views to an illustrative process for the preparation of a freeze-dried plasma cake from liquid human plasma, prior to insertion and storage within the device shown in FIG. 1.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Device for Storing and Reconstituting Freeze-Dried Plasma

Figure 1:
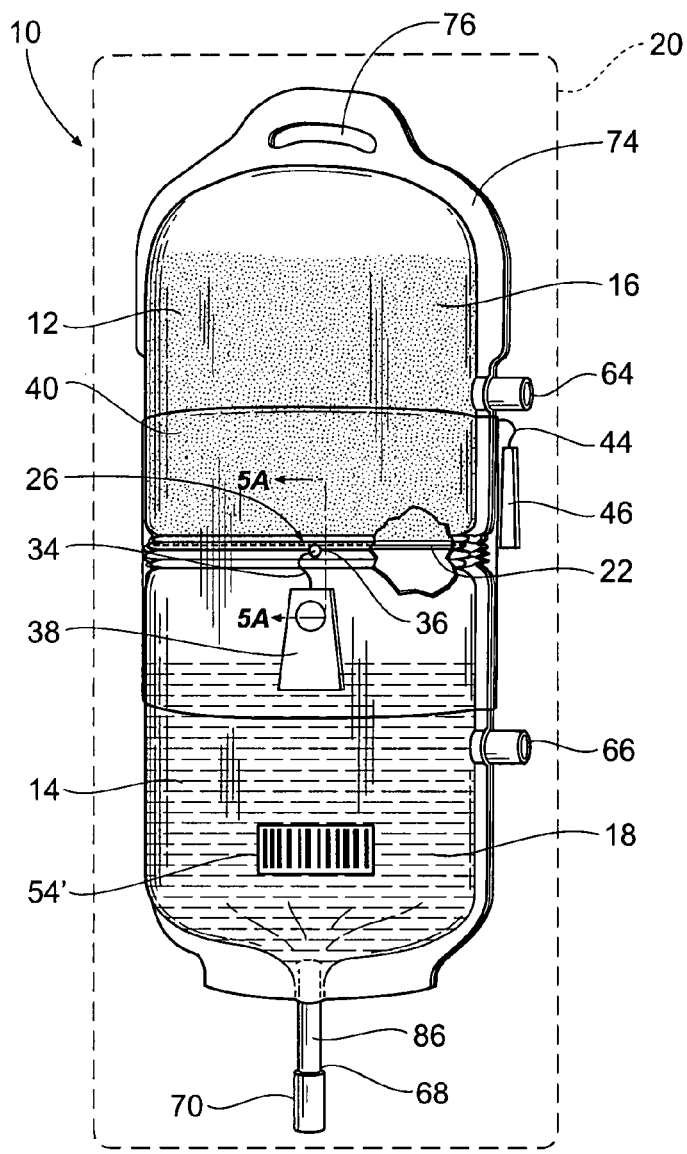
FIG. 1 is a front elevation view of a device for storing freeze-dried material, e.g., freeze-dried human plasma, and a reconstituting liquid for the freeze-dried material, making possible a reconstitution of the freeze-dried material within the device and an administration of the reconstituted freeze-dried material directly from the device to a recipient, the device being shown prior to the removal of an outer protective skirt.
Figure 2:
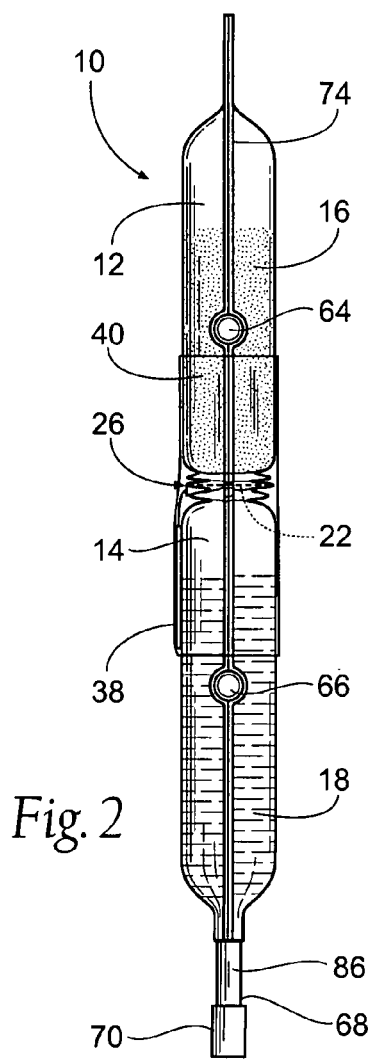
FIG. 2 is side elevation view of the device shown in FIG. 1.

FIGS. 1 and 2 show a device 10 for storing and administering a freeze-dried material. The device 10 comprises a flexible bag having a first collapsible chamber 12 and a second collapsible chamber 14.

The first chamber 12, also referred to as the dry chamber, contains an aliquot of a freeze-dried material 16. The nature and type of freeze-dried material 16 can vary. In the illustrated embodiment, the freeze-dried material comprises human plasma, and the aliquot is a single donor unit of human plasma.

The second chamber 14, also referred to as the wet chamber, contains a reconstituting liquid 18 for the freeze-dried material 16. The nature and type of the reconstituting material 18 can vary. In the illustrated embodiment, the reconstituting material 18 comprises degassed, sterile water. In use, the sterile water in the wet chamber 14 is mixed with the freeze-dried plasma in the dry chamber 12 to provide plasma for transfusion. The plasma is reconstituted and administered on site using the device 10.

The first chamber 12 is sized and configured to maintain the freeze-dried material 16, prior to its reconstitution, in a vacuum packed, aseptic, moisture-free and low concentration oxygen environment, preferably accommodating long term storage, e.g., at least 2 years at room temperature. Stored in this environment, the freeze-dried material 16 retains its desired qualities for transfusion.

The second chamber 12 is sized and configured to maintain the reconstituting liquid 18, prior to its mixing with the freeze-dried material 16, in an aseptic environment and at a low gas concentration, preferably accommodating long term storage, e.g., at least 2 years at room temperature.

The volume of each of the chambers 12 and 14 is preferably approximately 50% larger than the volume of the freeze-dried material 16 in the first chamber 12. This provides ample volume within the device 10 for mixing the freeze-dried material 16 and reconstituting liquid 18, either in the first chamber 12 or the second chamber 14, as will be described in greater detail later.

The device 10 may be made, e.g., of an inert medical grade plastic material, such as polyvinyl chloride, polyethylene, polypropylene, or high density polyethylene. The device 10 can comprise a multi-laminate of polymer layers for greater durability, e.g., to resist tearing and puncturing that could be encountered in normal handling.

The material of the device 10 can be selected to be transparent, if desired, to allow visual inspection of the contents of the chamber 12 and 14. The material in the first chamber 12 can be selected to provide a gas-impermeable barrier, such as a metallized, reduced gas-permeability coating, or a metal laminate. In this case, the wall of the first chamber may be opaque.

Furthermore, the device 10 may be enveloped prior to use by a vacuum sealed over-wrap 20 (shown in phantom lines in FIG. 1), made, e.g., a metallized, gas impermeable material. The over-wrap 20 enhances shelf-stability.

Figure 5A:
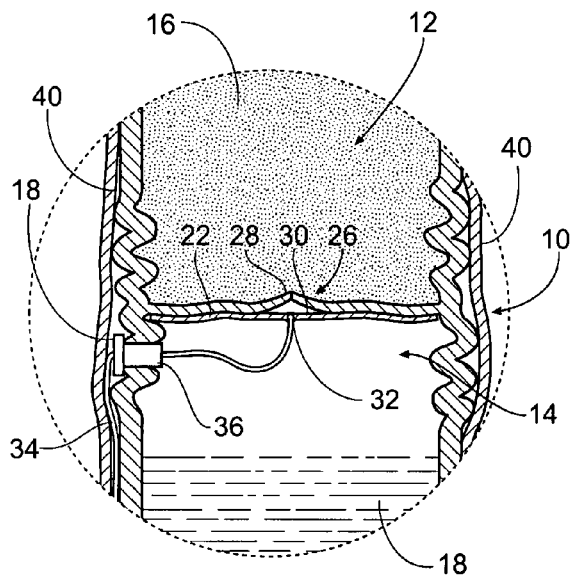
FIG. 5A is a side elevation section view of the interior sealing wall and associated valve assembly formed within the device taken generally along line 5A-5A in FIG. 1, prior to the removal of the outer protective skirt.

An interior sealing wall 22 (see FIG. 1) compartmentalizes the device 10 into the first and second chambers 12 and 14 (see also FIG. 5A). The sealing wall 22 provides a barrier between the first chamber 12 and the second chamber 14, which normally prevents contact between the freeze-dried material 16 and the reconstituting liquid 18 during storage, up to the instant of use.

As FIGS. 5A/B and 7 show, one or more regions 24 of the sealing wall 22 may be selectively opened by a caregiver, as will be described in greater detail later. The region(s) 24, when opened, make possible fluid communication between the two chambers 12 and 14. The fluid communication makes it possible to mix the reconstituting liquid 18 with the freeze-dried material 16, as will further be described in greater detail later.

Figure 5B:
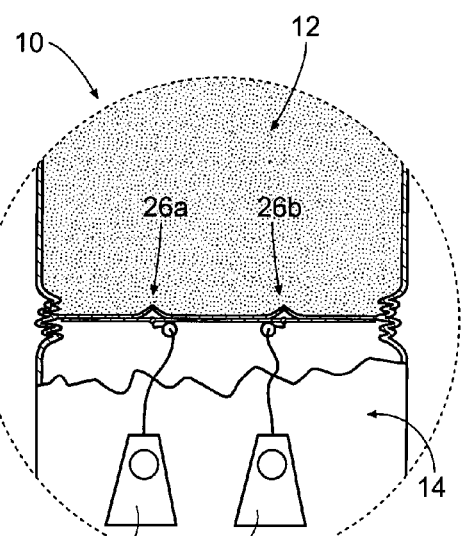
FIG. 5B is a side elevation section view like that shown in FIG. 5A, showing an alternative arrangement of the interior sealing wall and multiple valve assemblies.

The region(s) 24 of the sealing wall 22 may be opened in various ways. In a representative embodiment (see FIG. 5), the sealing wall 22 includes a normally closed valve assembly 26 associated with each region 24 where the sealing wall 22 is to be opened. In FIG. 5A, a single region 24 is shown, so a single valve assembly 26 is shown. As shown in FIG. 5B, where multiple regions 24a and 24b are provided, each region 24a and 24b would include its own dedicated valve assembly 26a and 26b, respectively.

In the representative embodiment (see FIGS. 5A and 5B), each valve assembly 26 includes a primary, pressure sensitive valve 28. The valve 28 can take the form, e.g., of a short duck bill or two way flap valve. The primary valve 28 is sized and configured to normally resist flow communication between the two chambers 12 and 14.

In the representative embodiment, each valve assembly 26 also includes a normally closed septum 30 between the valve 28 and the wet chamber 14. The septum 30 maintains closure between the two chambers 12 and 14, independent of the valve 28. Independent of the valve 28, the septum 30 prevents unintended passage of material between the two chambers 12 and 14, thereby maintaining the separate integrity of the freeze-dried material 16 and the reconstituting liquid 18 within the device 10 prior to use.

The septum 30 includes an integrated tear member 32 that is incorporated within the septum 30. The integrated tear member 32 is coupled to a pull string 34 that extends through a fluid sealed pass-through or septum 36 in the wall of the second chamber 14. As FIG. 1 shows, the pull string terminates outside the device 10 at a pull tab 38.

Figure 6:
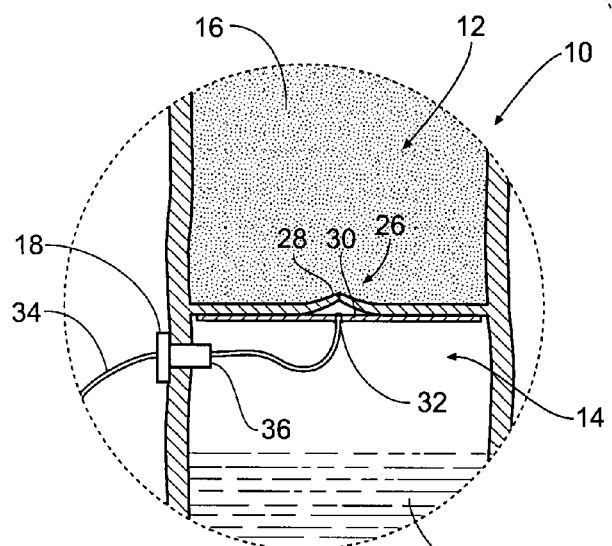
FIG. 6 is a side elevation section view of the interior sealing wall and associated valve assembly formed within the device taken generally along line 6-6 in FIG. 4A, after the removal of the outer protective skirt and prior to manipulating the device to reconstitute the freeze-dried materials.
Figure 7:
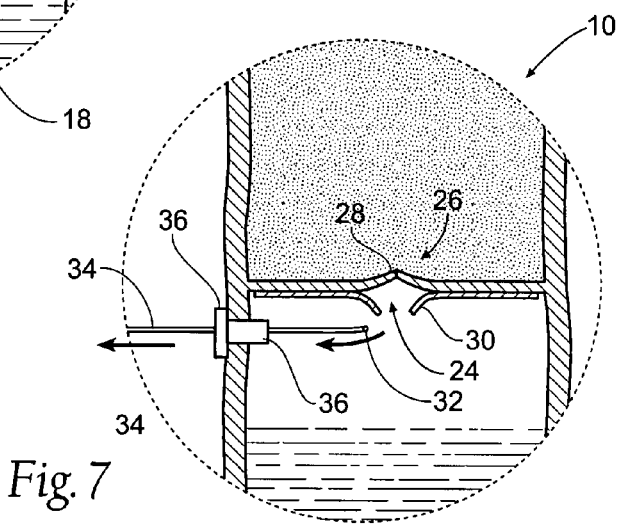
FIG. 7 is a side elevation section view of the interior sealing wall and associated valve assembly like that shown in FIG. 6, after opening at least one region of interior sealing wall and prior to manipulating the device to reconstitute the freeze-dried materials.

As FIGS. 6 and 7 show, the tear member 32 is sized and configured to open the septum 30 when a caregiver pulls on the tab 38. The pass-through or septum 26 seals around the pull string 34, and also seals close after passage of the pull string 34 from the interior of the chamber 14, maintaining in integrity of the second chamber 14. Opening the septum 30 in this manner forms the open region 24 (see FIG. 7). The open region 24 places the first and second chambers 12 and 14 into communication through the valve 28.

With the region 24 opened (see FIG. 7), the primary valve 28 still serves to normally resist flow communication between the two chambers 12 and 14. However, when the region 24 is opened, the valve 28 is sized and configured to resiliently yield in response to a difference in fluid pressure between opposite sides of the valve 38 (see FIGS. 11 and 14). In response to the pressure differential, the valve 28 opens in the direction of the fluid pressure differential, from the region of higher pressure toward the region of lower pressure.

As will be described in greater detail later (as shown, respectively, in FIGS. 10 and 13), the caregiver creates the fluid pressure differential across the valve 28 by selectively squeezing one chamber and not the other chamber. Fluid is expelled in response to the fluid pressure differential through the valve 28 from the chamber that is squeezed into the chamber that is not squeezed.

The multi-component valve assembly 26 provides a redundant sealing capability, to assure that the chambers 12 and 14 remain separated until it is desired to reconstitute the freeze-dried material 16.

In a representative embodiment (see FIGS. 1 and 2), the device 10 further includes an outer tear-away skirt 40, which provide further redundancy. As FIGS. 1 and 2 show, the skirt 40 overlays the device 10 in the region of the sealing wall 22. The skirt 40 serves to overlay and protect the components of the valve assembly 26 associated with the sealing wall 22.

At least one region of the skirt 40 is circumferentially attached about an exterior wall of the device, e.g., by adhesive, either in the region of the first chamber, the second chamber, or both. Furthermore, as the skirt 40 is installed about the device 10, the exterior wall of the device is desirably plicated or pleated or otherwise bunched together (as FIGS. 1 and 2 show). Alternatively, the placations can be performed in the wall of the container.

The placations relieve wall stress in the region of the sealing wall 22. The skirt 40, once attached, maintains these placations or pleats, and thereby serves to relieve or distribute wall stresses in the region of sealing wall 22 and the components of the valve assembly 26 associated with the sealing wall 22. Such wall stresses can arise, e.g., due to the weight of the reconstituting liquid 18 contained in the second chamber 14, and/or by virtue of handling during transport and manipulation prior to use. The presence of the overlaying skirt 40 also serves to isolate the components of the valve assembly 26 associated with the sealing wall 22 from unintended contact during transport and prior to use.

Figure 3:
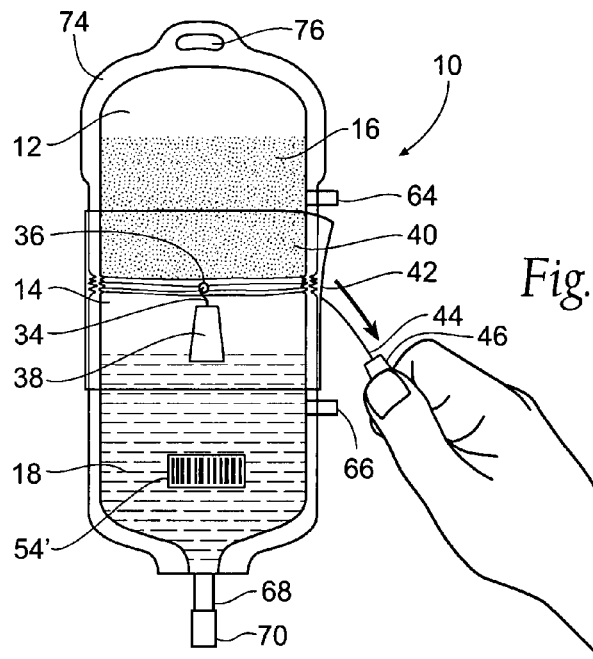
FIG. 3 is a front elevation view of the device shown in FIG. 1, showing the tearing of the outer protective skirt for its removal prior to manipulating the device to reconstitute the freeze-dried materials.
Figure 4A:
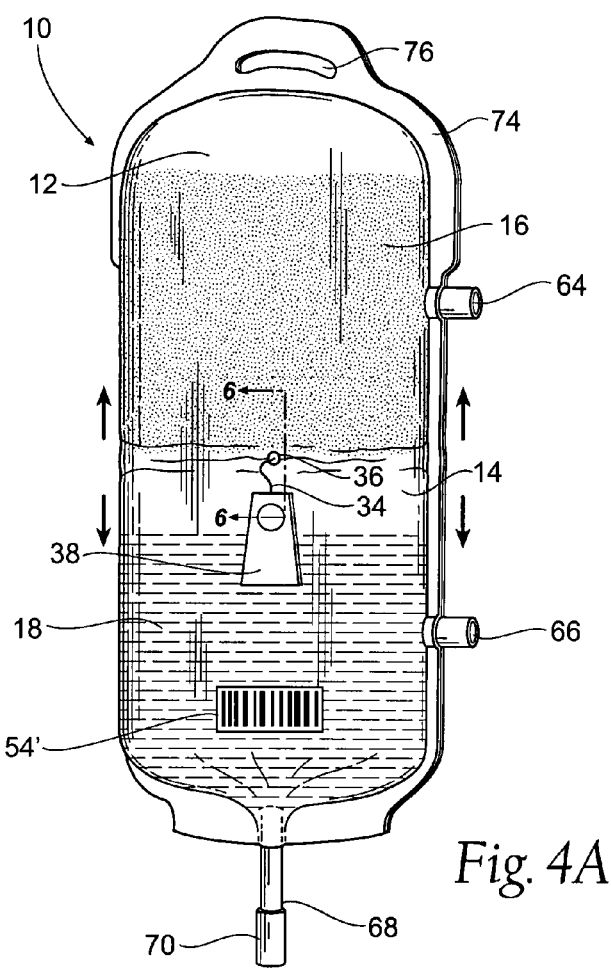
FIG. 4A is a front elevation view of the device shown in FIG. 3, after the removal of the outer protective skirt and prior to manipulating the device to reconstitute the freeze-dried materials.
Figure 4B:
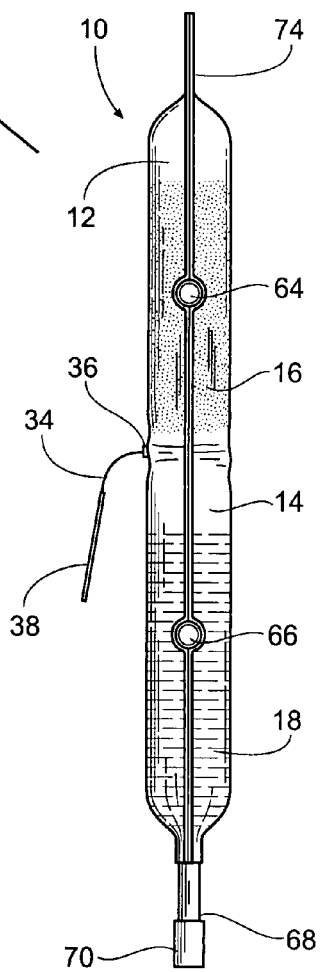
FIG. 4B is side elevation view of the device shown in FIG. 4A.

As FIG. 1 shows, the skirt 40 includes an integrated tear member 42. The integrated tear member 42 includes a pull string 44 that terminates with a pull tab 46, that depends outside the skirt 40. The tear member 42 is sized and configured to tear open the skirt 40 when a caregiver pulls on the tab 46 (as FIG. 3 shows). Upon removal of the skirt 40, the placations of the walls of the bags 12 and 14 are relieved (as FIGS. 4A and 4B show), placing the components of the valve assembly 26 associated with the sealing wall 22 into condition for manipulation.

It should be understood that reference to the first chamber 12 and the second chamber 14 is done to distinguish one chamber from the other, and not to limit either chamber to a specific spatial relationship. For example, the chambers 12 and 14 may be arranged face to face, having vertical edges in contact.

The technical features of the device 10 includes separate chambers or compartments that are separated by sealing means that will allow for eventual interconnection and intercommunication, between the chambers, which can be accomplished in various ways. Furthermore, reference to a bag or chambers should not be limited to any specific structure or shape but should be understood to refer any container capable of carrying and mixing the contents 16 and 18.

II. Preparing and Packaging the Freeze Dried Material and Reconstituting Liquid

Preparing and packaging the freeze-dried material 16 and reconstituting liquid 18 comprises two main processing steps: (i) freeze-drying the material 16, and (ii) packaging the material 16 and the reconstituting liquid 18 within the chambers 12 and 14.

A. Preparation of Freeze-Dried Plasma

In a representative embodiment, the freeze-dried material 16 comprises plasma. A description of an illustrative way of preparing freeze-dried plasma for packaging in the device 10 therefore follows.

Preparation and manufacturing of the plasma will take place in a sterile setting. Preferably, manufacturing and preparation procedures will be done in an ISO Class 5 clean room (or better) with ISO Class 3 bio-containment hoods for aseptic handling of human plasma. Freeze drying will be done aseptically in a CIP/SIP freeze dryer.

Human plasma is collected from a single donor in a conventional way, e.g., by collecting a unit of whole blood from the donor in a closed system collection bag, followed by centrifugal separation of the plasma and its collection in an integrally connected transfer bag (containing one plasma unit of about 250 ml). Each unit (contained in the transfer bag) will be handled individually in the bio-containment hood. Between handling one single donor unit and another unit single donor unit from a different donor, there will be a line clearance protocol for change-over in the bio-containment hood. This protocol will address removal of all tools and materials associated with the previous handling. It will also address the thorough wash down of the containment work area and work area instruments (mass balances) to ensure no residues of the previous handling were left in place. The identification of single donor samples will be maintained by bar coding and other tagging of the single donor human plasma containers.

As shown in FIG. 17A, prior to freeze drying, the 250 ml human plasma unit is dispensed from the transfer bag 48 into a sterile, pyrogen free, rectangular mold 50 (e.g., 4 cm×10 cm×12.5 cm—d×w×l). The mold 50 can be stainless-steel; however it can also be composed of metal with good thermal transfer properties such as aluminum, aluminum alloy, titanium or gold. The mold 50 may be coated on its inside surfaces with a tough, inert barrier film with good release properties such as PTFE or diamond.

As shown in FIG. 17B, the mold 50 containing the human plasma is then placed inside a water-impermeable, vapor-permeable, sterile, heat sealable bag 52 with bar coding and tagging 54 indicative of the human plasma identification (source, blood type, date of collection, etc.). This vapor permeable bag 52 would typically be manufactured using microporous PTFE membrane material (e.g. Gore-Tex™) or microporous HDPE membranes (e.g. Tyvek™).

The bag 52 is heat sealed to contain the mold 50 and human plasma. The bag 52 is designed to neatly contain the mold 50 and its contents without any bunching or sagging of the bag material below the surface of the interior mold wall edge or at the base of the mold.

As shown in FIG. 17C, the mold 50 inside the containment bag 52 is then placed inside a freeze dryer 56 on an aseptic freeze dryer shelf surface 58. The freeze dryer 56 used for the lyophilization will be a validated clean in place, steam in place freeze dryer with shelf area of near 200 square feet or more. Such a freeze dryer 56 can accommodate at least 500 molds when it is fully loaded.

Once loaded, the freeze dryer cycle is started. This cycle generally cools the human plasma to near −45° C. and freezing for 2 to 8 hours, followed by cooling of the freeze dryer condenser and application of vacuum to start the freeze drying cycle. A freeze-dried human plasma cake 60 is formed.

In the primary freeze drying cycle, the temperature of the human plasma cake 60 needs to remain below −33° C. (the collapse temperature) to maintain its integrity. When the moisture content of the cake 60 is below 5% weight per weight (w/w), a secondary drying cycle (the elevated temperature) is used to further lower the moisture content. Generally the combined primary and secondary freeze drying cycles will take at least 72 hours. At the conclusion of the freeze drying cycle, the freeze dryer vacuum is opened to an atmosphere of an oxygen-free, high purity inert gas such as nitrogen or argon.

Figure 17D:
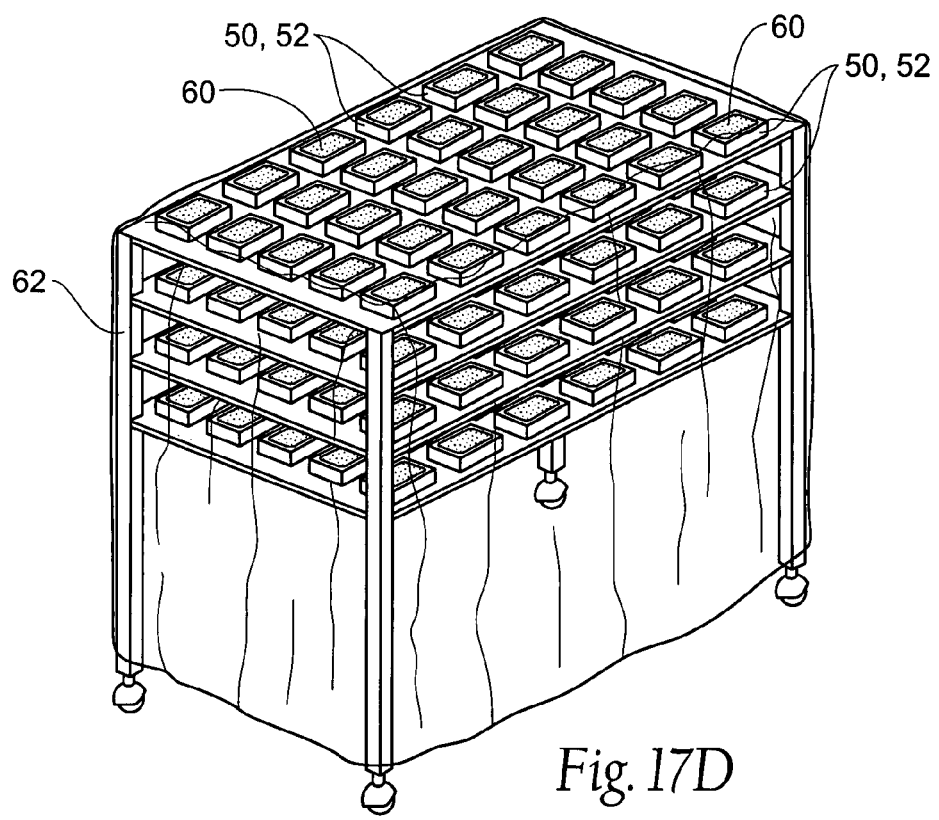

As shown in FIG. 17D, the freeze dried cakes 60 in their molds 50 and containment bags 52 are removed to an aseptic containment cart 62 whose environment may be maintained under a nitrogen or argon blanket to exclude moisture and oxygen. The containment cart 62 may couple to the front of the freeze dryer to allow for transfer of the freeze dryer contents under a controlled inert gas blanket.

The containment carts 62 may be used to store human freeze dried plasma cakes (each cake within a mold 50 and enclosed within a bag 52) as well as allow cakes to be transferred to a device loading area, which allows loading of the freeze dried plasma cake 60 into the device 10, as will be described in greater detail later.

B. Packaging Freeze-Dried Plasma and Water into the Device

As shown in FIG. 1, the device 10 comprises a first aseptic vacuum port 64, which communicates with the first chamber 12, and a second aseptic vacuum port 66, which communicates with the second chamber 14. The vacuum ports 64 and 66 are sized and configured for connection to various tubing T during final assembly (see FIGS. 18 to 21) to facilitate packaging of the freeze-dried plasma material 16 and reconstituting liquid 18 (e.g., water) within the device 10.

An administration port 68 is also heat sealed in communication with the second chamber 14. The administration port 68 is used during the packaging process to convey the reconstituting liquid 18 into the second chamber 14, as will be described in greater detail later. After the reconstituting liquid 18 is packaged within the chamber 14, the administration port 68 is sealed with a conventional septum or frangible membrane assembly or a convention screw-lock luer fitting 70, to accommodate its coupling to an administration set 72 to the port 28 at time of transfusion, as shown in FIG. 16.

Figure 18:
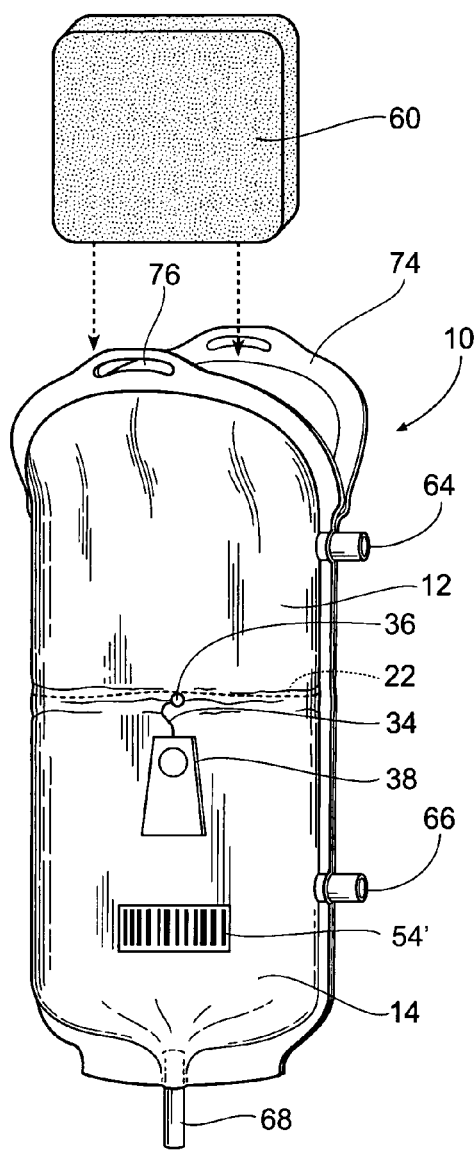
FIGS. 18 and 19 are front elevation views of placing a freeze-dried material (like the plasma cake formed using the process FIGS. 17A to 17E) in the first chamber of the device shown in FIG. 1.
Figure 19:
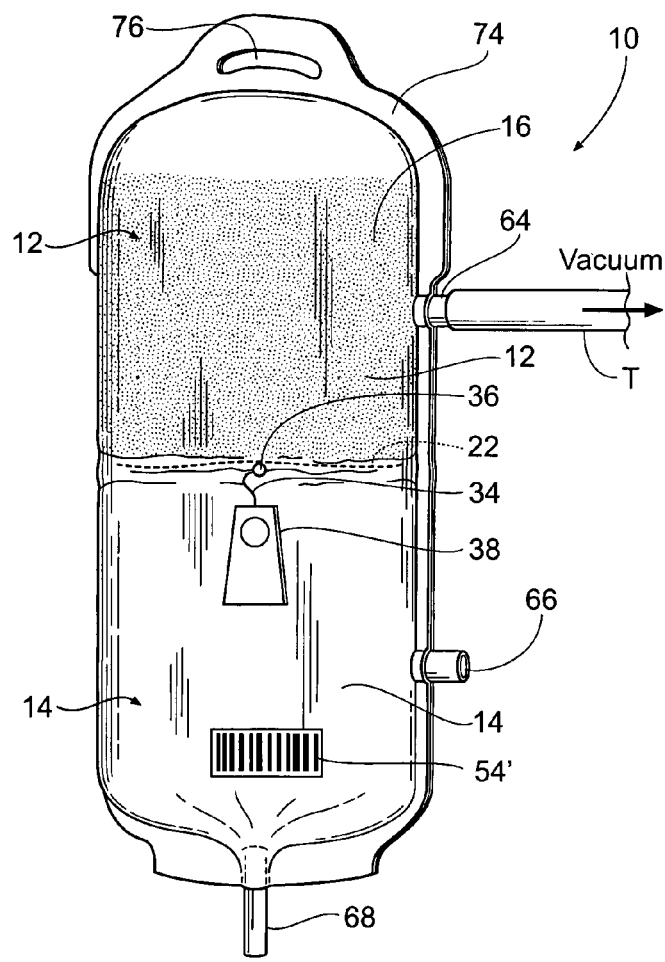

The device 10 also comprises a heat sealable aseptic flange 74 (see FIG. 1), which allows a freeze-dried plasma cake 60 to be inserted into the first chamber 12, as shown in FIG. 18, and then sealed in a sterile fashion, as shown in FIG. 19.

A slot 76 may be pre-formed on the flange 74. The slot 76 makes it possible to hang the device 10 at a desired gravity head height for administering reconstituted plasma to an individual, as FIG. 16 shows.

Individual single donor human plasma freeze dried cakes 60 are aseptically loaded into the device 10 (see FIG. 18) through the flange 74. The device loading area may be, e.g., a bio-containment hood that excludes significant oxygen and moisture contamination by inert gas blanketing. Also the device loading area may be an aseptic glove-box system with an inert gas environment.

Figure 17E:
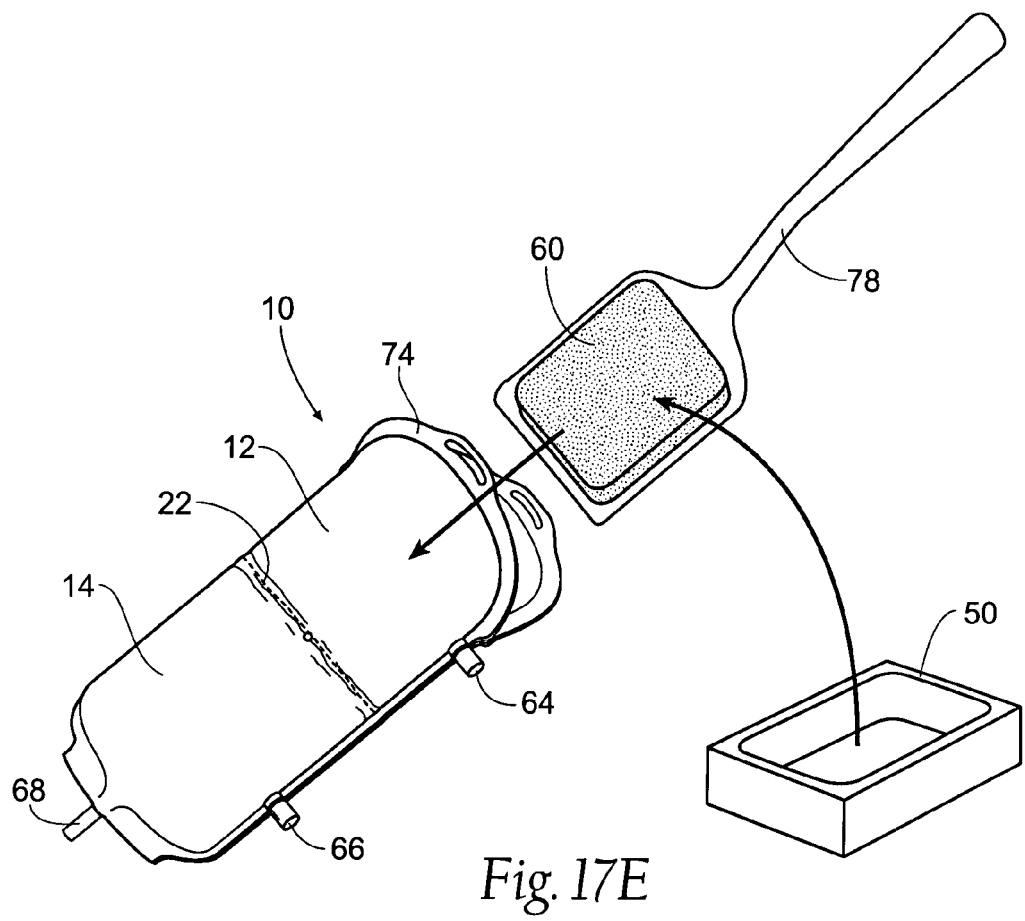

FIGS. 18 and 19 depict a representative loading process. The bag 52 is opened, and the plasma cake 60 removed from the mold 50. The plasma cake 60 is loaded through the open flange 74 into the first chamber 12. As shown in FIG. 17E, it is anticipated that the plasma cake 60 can be transferred into the chamber 12 directly from the mold 50 (after removal of the bag 52) using a single-use, aseptic, clear-plastic applicator tool 78, similar to a large open-ended spatula. Once the chamber 12 is loaded, the flange 74 can be sealed closed using various conventional aseptic techniques, e.g., dielectric welding or heat sealing.

The loading of the plasma chamber 12 can be through an "oyster style" opening that comprises approximately 50% of the flange 74 of the chamber 12, which can be readily sealed close after loading. An oyster opening would allow loading of the plasma cake 60 without concerns of damaging the first chamber 12 or the freeze-dried plasma during the process. In the case of the oyster opening, there would be sufficient excess overlay of the edge seam to allow for straightforward edge-seam alignment and contact during the sealing process.

Preferably, after loading and sealing of the chamber 12, an aseptic vacuum is applied through tubing T connected to the vacuum port 64 on the first chamber 12 (see FIG. 19). Upon achieving near 100 mTorr of pressure, the vacuum port 64 is heat sealed and the tubing T removed. This evacuation process provides for the eventual ability to mix and reconstitute the human freeze dried plasma without introduction of bubbles and without foaming. The vacuum would also cause the plasma cake 60 to be compacted to a fine powder, forming the freeze-dried material 16 within the chamber 12.

To maintain a direct traceable link between the source plasma and the material 16 packaged into the chamber 12, the device 10 preferably includes a bar coding and tagging 54' (see FIG. 1), which is indicative of the human plasma identification (source, blood type, date of collection, etc.), and which replicates or is otherwise linked to the bar coding and tagging 54 placed on the bag 52 enveloping the mold 50 at the time of freeze-drying. In this way, the device 10 maintains a traceable link back to the human donor source.

To assist in the reconstitution of the freeze dried plasma material 16, an aseptic dense sphere of an inert material such as, but not limited to, glass, polyvinyl chloride or high density polyethylene may be added to the inside of the chamber 12 prior to its closure.

Figure 20:
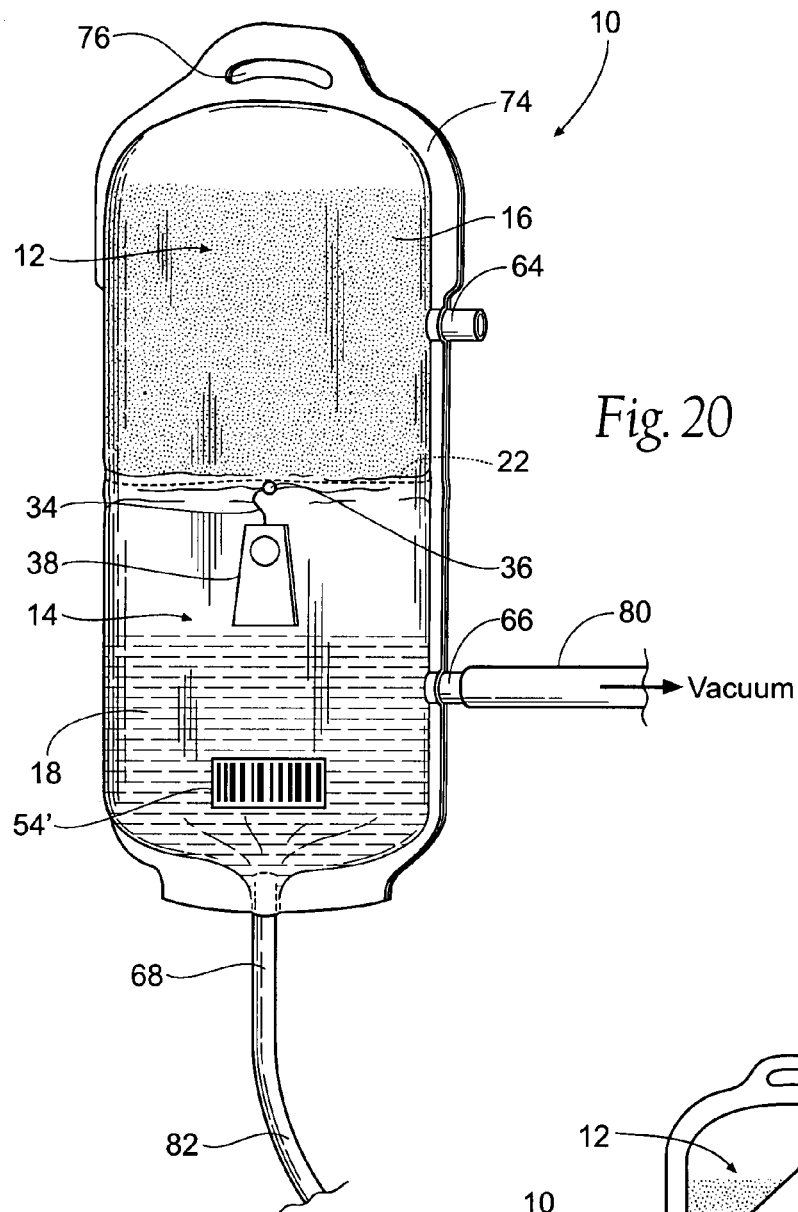
FIG. 20 is a front elevation view of placing a reconstituting liquid for the freeze-dried material in the second chamber of the device shown in FIG. 1.

The reconstituting liquid 18 (in the representative embodiment, gas-free water) is introduced into the second chamber 14. The vacuum port 66 and administration port 68 are connected to feed lines 80 and 82, respectively, as FIG. 20 shows. Gas in the chamber 14 is removed by application of aseptic vacuum.

The vacuum port 66 is sealed and the tubing 80 is removed. The required aliquot (e.g., approximately 250 ml) of degassed water for injection is added to the chamber 14 through the administration port 68. The tubing 82 is removed and the administration port 68 is then sealed with the conventional septum or frangible membrane assembly or a convention screw-lock luer fitting 70, which accommodate coupling of the administration set 68 to the port 68 at time of transfusion.

To assist in the reconstitution of the freeze dried plasma, an aseptic dense sphere of an inert material such as, but not limited to, glass, polyvinyl chloride or high density polyethylene may be present inside the second chamber 14.

Figure 21:
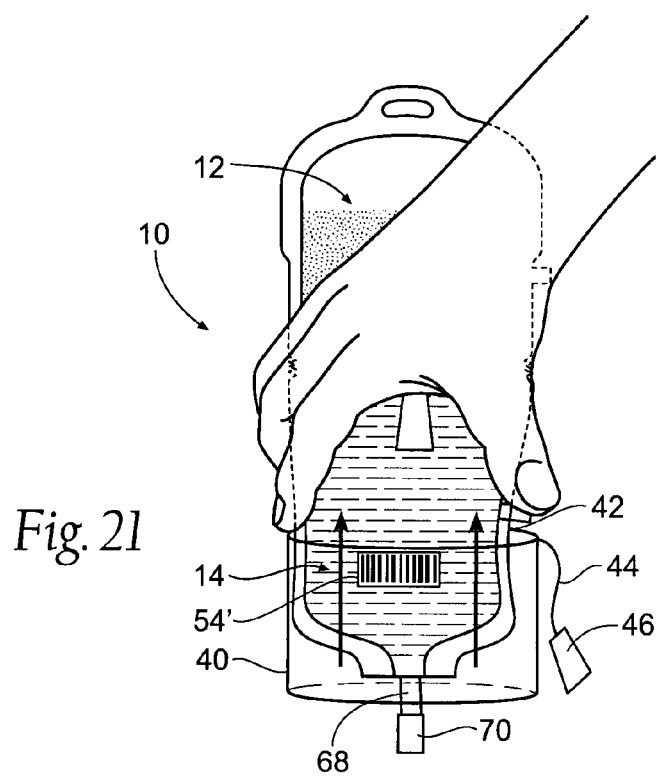
FIG. 21 is a front elevation view of placing the outer protective sleeve about the device, to create the device shown in FIG. 1.

As FIG. 21 shows, after packaging the freeze-dried material 16 and the reconstituting liquid 18 in the manner just described, the wall of the device 10 is plicated in the region of the sealing wall 22, as previously described, and the outer skirt 40 attached. The overwrap 20 can be applied, as shown in FIG. 1, if desired.

The device 10 is ready for storage, transport, and use

III. Reconstitution and Administration of the Freeze-Dried Material

The device 10 makes possible a purposeful two step manipulation in anticipation of reconstituting the freeze-dried material 16.

Figure 8:
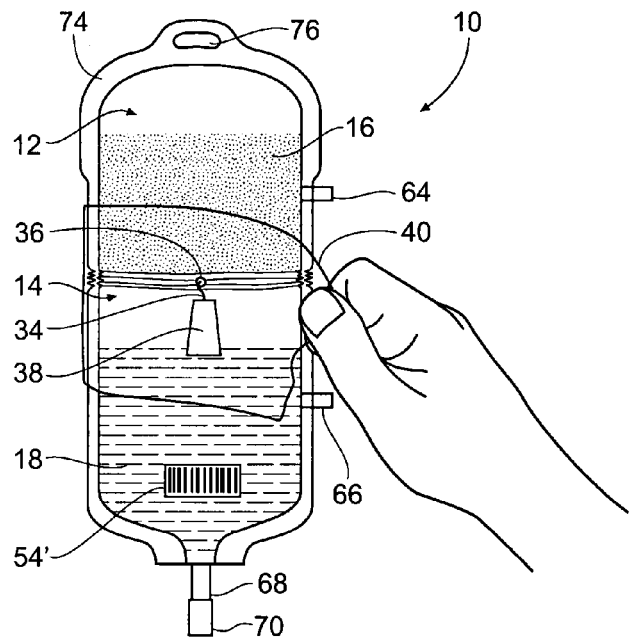
FIG. 8 is a front elevation view of the device shown in FIG. 1, showing the removal of the outer protective skirt prior to manipulating the device to reconstitute the freeze-dried materials.
Figure 9:
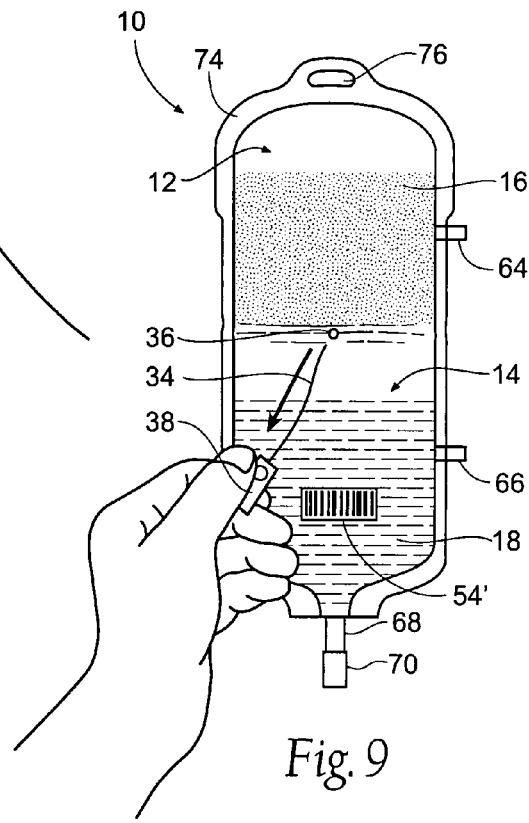
FIG. 9 is a front elevation view of the device shown in FIG. 8, showing the manipulation of the valve assembly to open at least one region of the interior sealing wall, in the manner also shown in FIG. 7.

In the first step (shown in FIG. 8), the tear member 42 is pulled to open and remove the skirt 40, which places the sealing wall 22 of the device 10 in the ready for use configuration shown in FIG. 6. In the second step (shown in FIG. 9), the tear member 32 is pulled to open the septum 20 (which FIG. 7 shows in greater detail). The region 24 of the sealing wall 22 is thereby opened.

Figure 10:
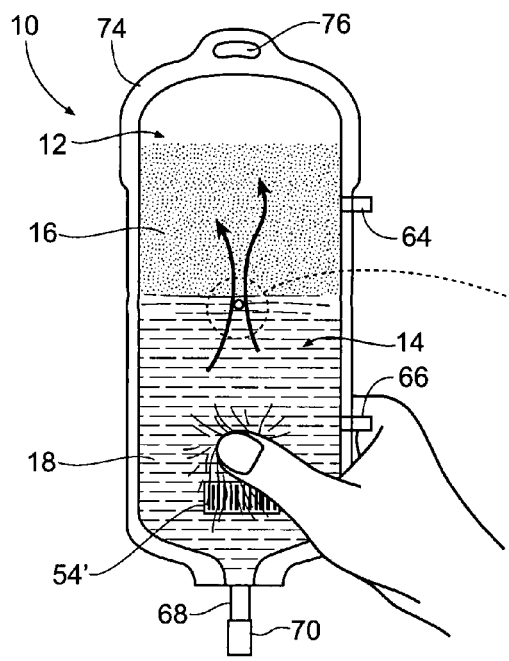
Figure 11:
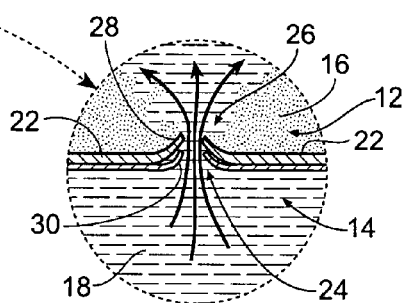

When the region 24 is opened, the caregiver can apply pressure to the second chamber 14 to express the reconstituting liquid 18 from the second chamber 14 into the first chamber 12 (see FIGS. 10 and 11), thereby beginning the reconstitution of the freeze-dried material 16. More particularly, with the region 24 opened, the caregiver can apply pressure to the second chamber 14 (as FIG. 10 shows) and not the first chamber 12. As FIGS. 10 and 11 show, the pressure differential between the second chamber 14 and the first chamber 12 expels the liquid 18 from the second chamber 14, through the valve 28 (which yields in response to the pressure differential to open in the direction of the first chamber 12, as FIG. 11 shows), and into the first chamber 12. The expelled liquid 18 mixes with the freeze-dried material 16 in the first chamber 12, beginning the reconstitution.

As FIG. 12 show, shaking the device 10 accelerates the mixing of liquid 18 and freeze-dried material 18 in the first chamber 12.

When the region 24 is opened, the caregiver can subsequently apply pressure to the first chamber 12 to express the material 16, now at least partially reconstituted in the liquid 18, from the first chamber 12 into the second chamber 14 (see FIGS. 13 and 14). Reconstitution of the freeze-dried material 16 is advanced. More particularly, as FIG. 13 shows, the caregiver can now apply pressure to the first chamber 12 (as FIG. 13 shows) and not the second chamber 14. As FIGS. 13 and 14 show, the pressure differential between the first chamber 12 and the second chamber 14 expels the mixture of the liquid 18 and the freeze-dried material 16 from the first chamber 12, through the valve 28 (which yields in response to the pressure differential to open in the direction of the second chamber 14, as FIG. 14 shows), and back into the second chamber 14. The expelled liquid 18 continues to mix with the freeze-dried plasma material 18, furthering the reconstitution of the material 18.

As FIG. 15 shows, shaking the device 10 further accelerates the mixing of water and freeze-dried plasma in the second chamber 14.

The material 16 reconstituted in the liquid 18 can be passed back and forth between the two chambers 12 and 14 by alternating pressure on the chambers 12 and 14, with intermediate shaking, until the desired degree of mixing occurs, at which time the mixture is ready for transfusion. More particularly, the caregiver can proceed to squeeze one chamber and not the other, to expel the mixture of the liquid 18 and freeze-dried material 18 back and forth between the chambers 12 and 14, with periodic shaking, until the desired degree of mixing and reconstitution of the plasma is accomplished.

At this point (as FIG. 16 shows), the caregiver can couple the administration fitting 70 of the device 10 to the fluid administration set 72. The reconstituted plasma is transfused by gravity flow through a phlebotomy needle 84 into the circulatory system of an individual.

The administration fitting 70 can further include a static mixing tube 86 (as shown in FIG. 16), to assist in continued reconstitution of plasma aliquot 5 with water 7 during transfusion.

The device 10 as described provides:

i) long term stable containment of a freeze-dried material such as freeze-dried human plasma;

ii) eventual rapid reconstitution of the freeze-dried material with a reconstituting liquid for injection; and iii) eventual delivery of the reconstituted freeze dried material to a trauma victim in a safe, sterile manner.

IV. Other Representative Embodiments

A. Dual Containers With Intermediate Valve Passage

Figures 22, 23:
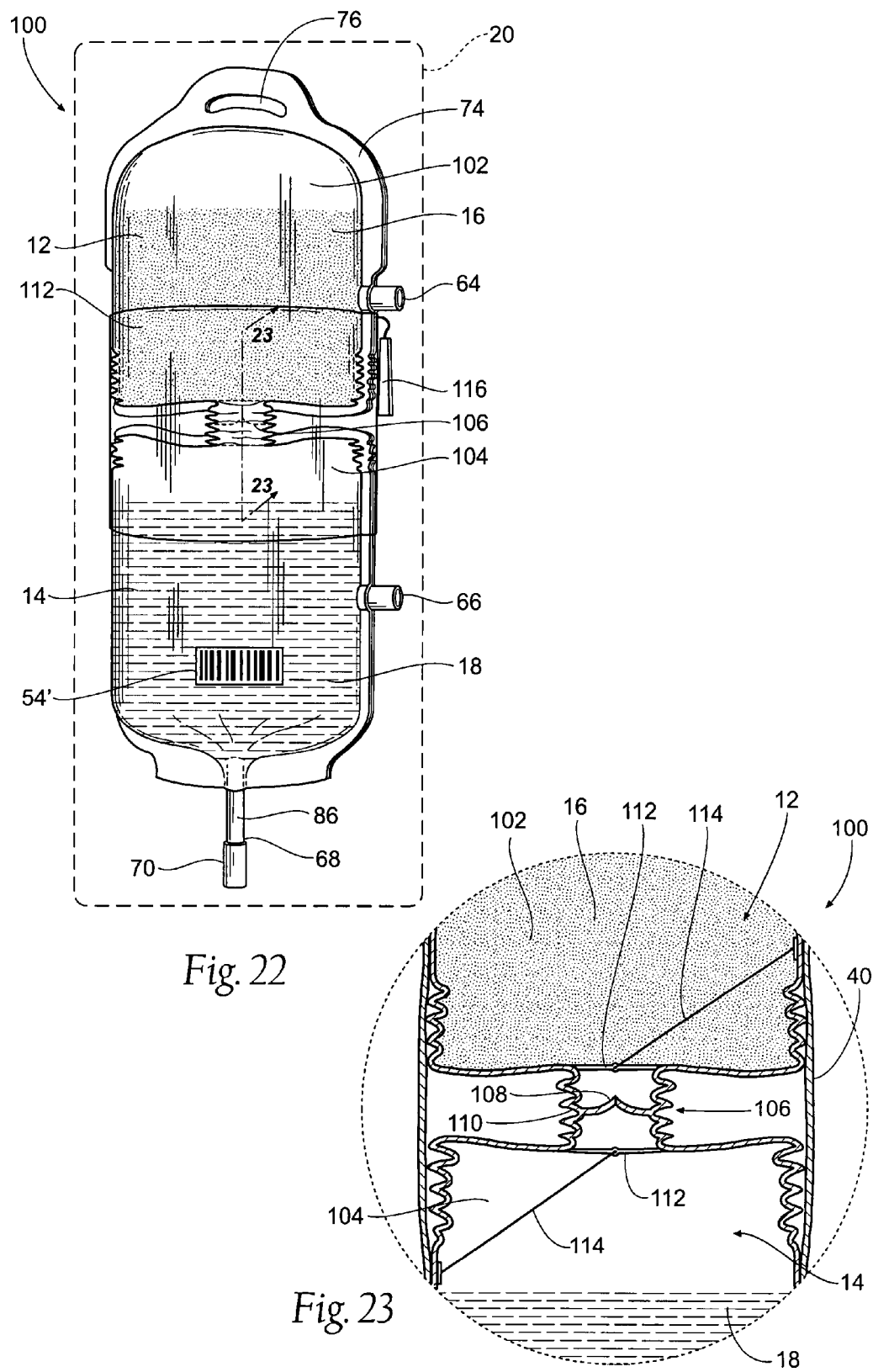
FIG. 22 is a front elevation view of an alternative device for storing freeze-dried material, e.g., freeze-dried human plasma, and a reconstituting liquid for the freeze-dried material, making possible a reconstitution of the freeze-dried material within the device and an administration of the reconstituted freeze-dried material directly from the device to a recipient, the device being shown prior to the removal of an outer protective skirt.
FIG. 23 is a front elevation interior section view of the valve assembly formed in the device taken generally along line 23-23 in FIG. 22, prior to the removal of the outer protective skirt.

FIG. 22 shows another representative embodiment of a device 100 for storing an administering a freeze-dried material. The device 100 comprises a first collapsible container 102 and a second collapsible container 104, joined by an intermediate normally closed valve assembly 106.

The device 100 shares many of the technical features of the device shown in FIG. 1, albeit the particular structure differs. The first container 102 comprises the dry chamber 12 as previously described, and is sized and configured to contains an aliquot of a freeze-dried material 16, such as a freeze-dried single donor unit of human plasma.

The second container 104 comprises the wet chamber 14, as previously described, and is sized and configured to contain a reconstituting liquid 18 for the freeze-dried material 16. As before described, the reconstituting material 18 can comprise, e.g., degassed, sterile water.

In use, the sterile water in the wet chamber 14 is mixed with the freeze-dried plasma in the dry chamber 12 to provide plasma for transfusion. The plasma is reconstituted and administered on site using the device 10.

As before described, the first container 102 is sized and configured to maintain the freeze-dried material 16, prior to its reconstitution, in a vacuum packed, aseptic, moisture-free and low concentration oxygen environment, preferably accommodating long term storage, e.g., at least 2 years at room temperature. Stored in this environment, the freeze-dried material 16 retains its desired qualities for transfusion.

As also before described, the second container 104 is sized and configured to maintain the reconstituting liquid 18, prior to its mixing with the freeze-dried material 16, in an aseptic environment and at a low gas concentration, preferably accommodating long term storage, e.g., at least 2 years at room temperature.

The volume of each of the containers 102 and 104 is preferably approximately 50% larger than the volume of the freeze-dried material 16 in the first chamber 12. This provides ample volume within the device 10 for mixing the freeze-dried material 16 and reconstituting liquid 18, either in the first container 102, or the second container 104, as will be described in greater detail later.

The containers 102 and 104 may be made, e.g., of an inert medical grade plastic material, such as polyvinyl chloride, polyethylene, polypropylene, or high density polyethylene. One or both of the container 102 and 104 can comprise a multi-laminate of polymer layers for greater durability, e.g., to resist tearing and puncturing that could be encountered in normal handling.

The material of the containers 102 and 104 can be selected to be transparent, if desired, to allow visual inspection of the contents of the chamber 12 and 14. The material in the first container 102 can be selected to provide a gas-impermeable barrier, such as a metallized, reduced gas-permeability coating, or a metal laminate. In this case, the wall of the first chamber may be opaque.

As before described, the device 100 may be enveloped prior to use by a vacuum sealed over-wrap 20 (shown in phantom lines in FIG. 22), made, e.g., a metallized, gas impermeable material. The over-wrap 20 enhances shelf-stability.

In the alternative representative embodiment shown in FIG. 22, the valve assembly 106 includes a pressure sensitive valve 108 enclosed within a flexible tubular valve passage 110, which extends between the two containers 102 and 104. The valve 108 can take the form, e.g., of a short duck bill or two way flap valve. The valve 108 is sized and configured to normally resist flow communication between the two containers 102 and 104. However, the valve 108 is sized and configured to resiliently yield in response to a difference in fluid pressure between opposite sides of the valve 108 (in the same manner as the valve 28 shown in FIGS. 11 and 14). In response to the pressure differential, the valve 108, like the valve 28, opens in the direction of the fluid pressure differential, from the region of higher pressure toward the region of lower pressure.

The regions of the wall of the containers to which the valve passage 11Q is joined normally close communication between the containers 102 and 104 through the valve passage 110.

An outer tear-away skirt 112 is wrapped around the mid-regions of the containers 102 and 104 and the intermediate valve passage 110. The skirt 112 serves to overlay and protect the components of the valve assembly 106 prior to use. At least one region of the skirt 112 is circumferentially attached about an exterior wall of each container 102 and 104, e.g., by adhesive, either in the region of the first chamber, the second chamber, or both.

As FIG. 23 shows, within the outer skirt 112, the mid-regions of the containers 102 and 104, and the valve passage 110 itself, are desirably plicated or pleated or otherwise bunched together, shortening the length of each container 102 and 104 and the valve passage 110. Alternatively, the placations can be performed in the walls of the containers 102 and 104 and/or valve passage 110. The presence of the overlaying skirt 112 serves to isolate the valve passage 100 from unintended contact during transport and prior to use.

As FIG. 23 shows, the walls of each container 102 and 104 that overlay opposite ends of the valve passage 110 each includes an integrated tear member 112. As FIG. 23 shows, each integrated tear member 112 is coupled by an internal pull string 114 to an adjacent side wall of the respective container 102 and 104. The internal pull string 114 is normally held in slight tension when the device 100 is in the plicated condition shown in FIG. 22 (i.e., when the mid-regions of the containers 102 and 104, and the valve passage 110 itself, are plicated and held in this condition by the outer shirt 112). When the device 100 is in the plicated condition, the tension on the internal pull string 114 is not sufficient to affect the tear member 112. The walls of each container 102 and 104 that overlay opposite ends of the valve passage 110 remain closed. When the device 100 is in the plicated condition, the chambers 12 and 14 and their contents remain isolated and separated prior to use.

Figure 24:
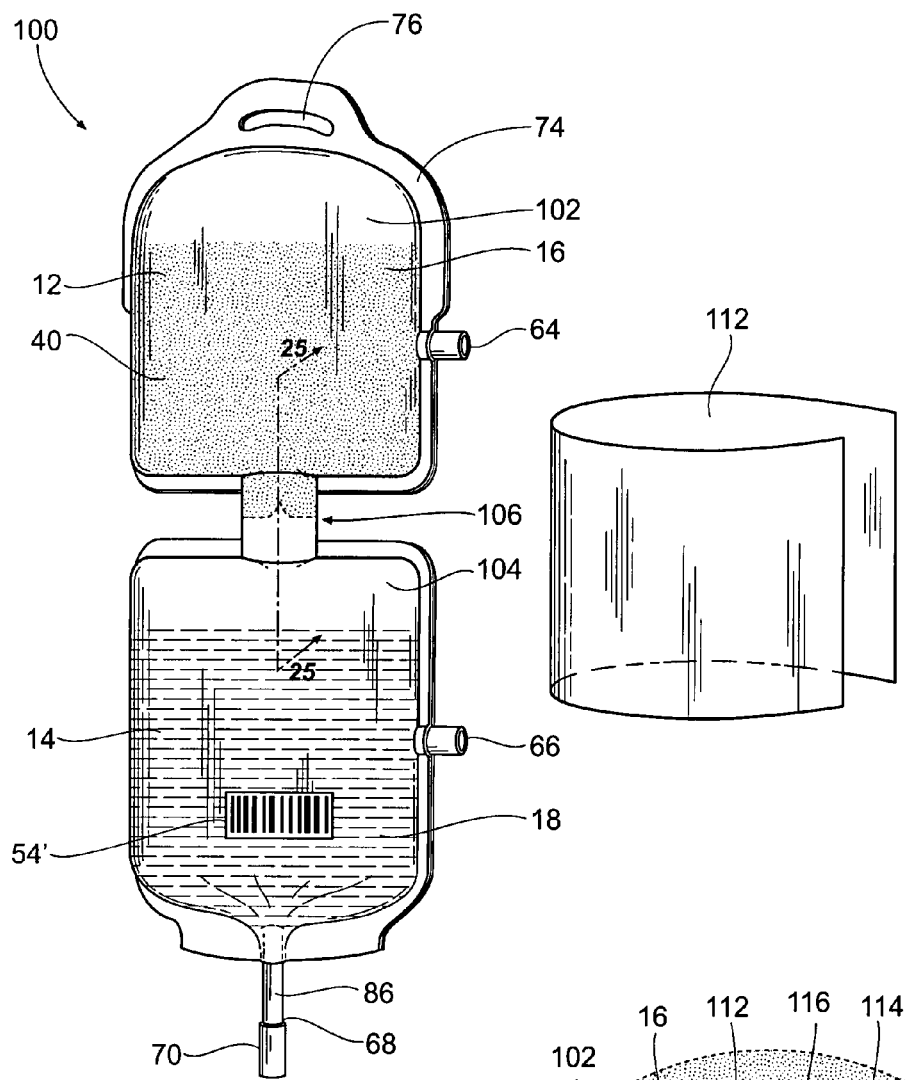
FIG. 24 is a front elevation view of the device shown in FIG. 22, after the removal of the outer protective skirt and prior to manipulating the device to reconstitute the freeze-dried materials.

As FIG. 24 shows, the skirt 112 can be torn and removed by operation of an integrated tear member 116 (in the manner shown in FIG. 3), to place the device 100 in the condition shown in FIG. 24. As FIG. 24 shows, upon removal of the skirt 112, the placations of the walls of the containers 102 and 104 and valve passage 110 are relieved, and the device 100 lengthens.

Figure 25:
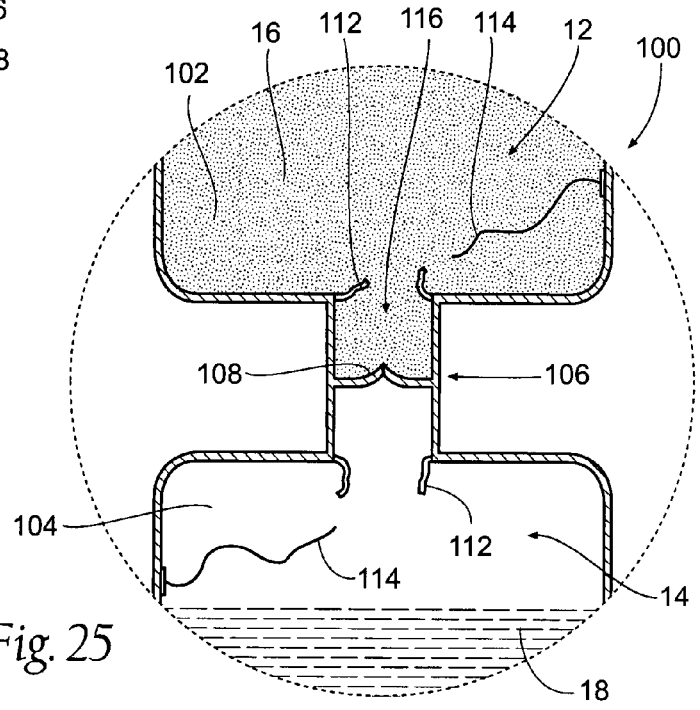
FIG. 25 is a front elevation interior section view of valve assembly like that shown in FIG. 23, taken generally along line 25-25 in FIG. 23 after removal of the outer protective skirt.

As FIG. 25 shows, when the device 100 lengthens, tension on the internal pull string 114 is increased. The increased tension is sufficient to activate the tear member 112, tearing open regions 116 of the walls on opposite ends of the valve passage 110 (as FIG. 25 shows). The open regions 116 place the first and second chambers 12 and 14 into communication through the valve passage 110.

Figure 26:
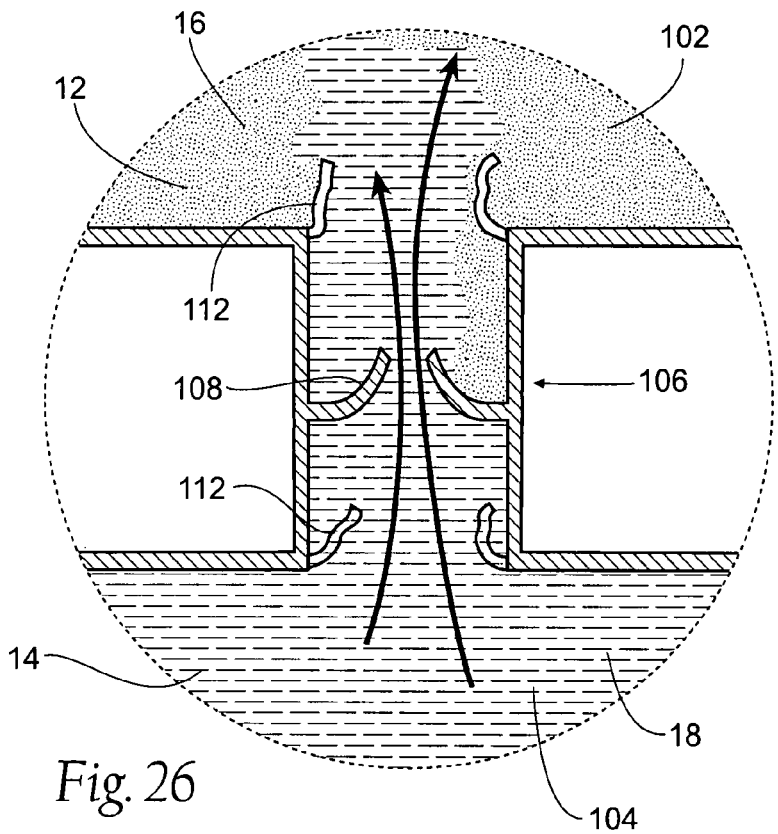
FIGS. 26 and 27 are front elevation interior section views showing the passage of materials through the valve assembly shown in FIG. 25 by manipulating the device to reconstitute the freeze-dried materials.
Figure 27:
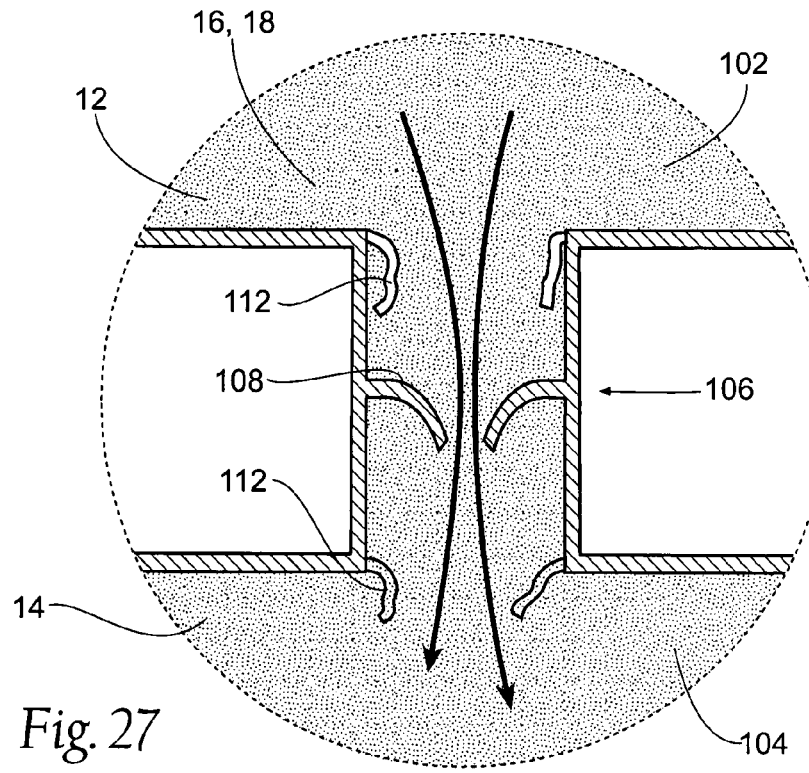

With the regions 116 opened, the caregiver can proceed to manipulate the device 100 in the same manner previously described with respect to device 10 (as shown in FIGS. 10 to 16). The caregiver creates the fluid pressure differential across the valve 108 by selectively squeezing one container and not the other container. Fluid is expelled in response to the fluid pressure differential through the valve 108 from the container that is squeezed into the container that is not squeezed to mix and reconstitute the freeze-drive material for administration. Transfer of materials in opposite directions between the chambers 12 and 14 through the valve passage 110 as a result of the manipulation of the containers 102 and 104 is shown in FIGS. 26 and 27.

B. Alternative Ways to Package the Reconstituting Liquid

Figure 28A:
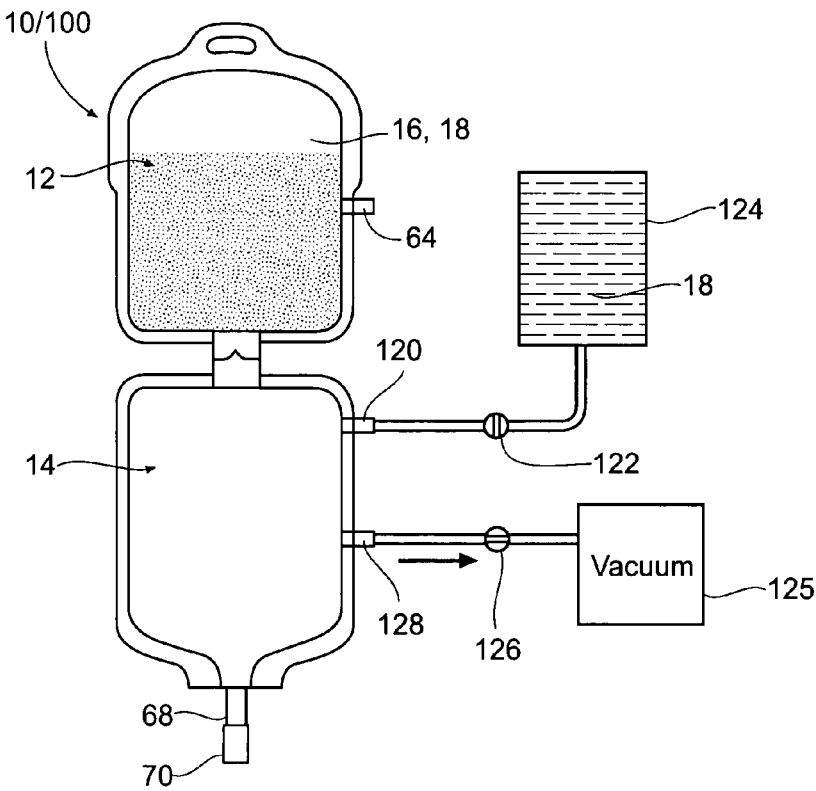
FIGS. 28A and 28B are a largely schematic views of an alternative way of packaging the reconstituting liquid for the freeze-dried material in the second chamber of the device of the type shown in FIG. 1 or 22.
Figure 28B:
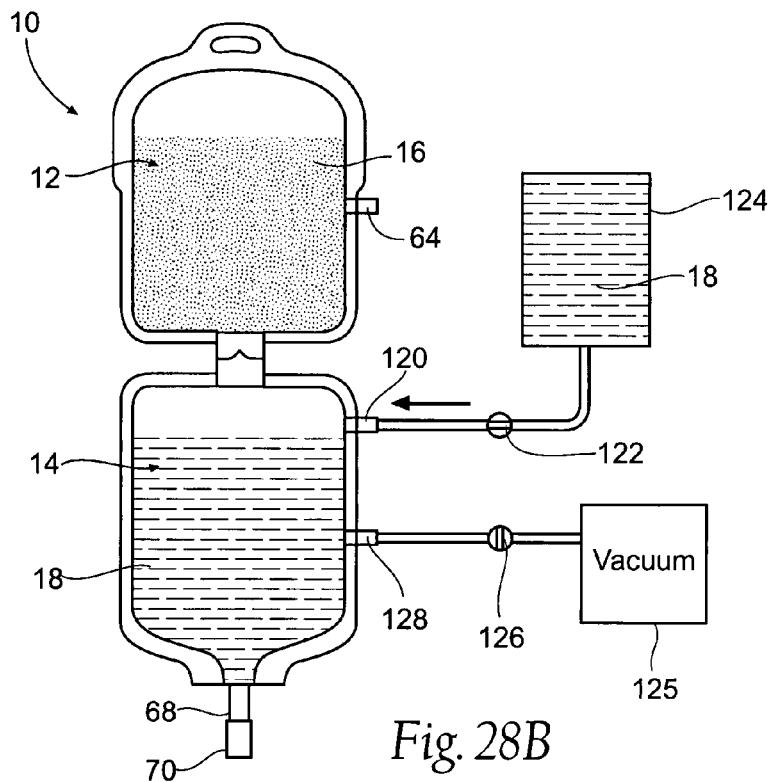

FIGS. 28A/B and 29A/B shows alternative ways to package the reconstituting liquid 18 in a device 10 or device 100 as previously described. In these alternative ways, it is not necessary to use the administration port 68 to convey the reconstituting liquid 18, but can be closed and sealed in a pre-packaging operation.

In one alternative representative embodiment (see FIG. 28A/B), the wet chamber 14 includes two packaging ports 120 and 128. In use (see FIG. 28A), the first port 120 is coupled to a source 124 of the reconstituting liquid 18 via a first inline valve 122. The second port 128 is coupled to a vacuum source 125 via a second inline valve 126.

As shown FIG. 28A, the first valve 122 is closed and the second valve 126 is opened. A vacuum is applied to the interior of the chamber 14. As shown in FIG. 26B, the first valve 122 is opened and the second valve 126 is closed. The reconstituting liquid 18 is conveyed by gravity flow into the chamber 14. Both packaging ports 120 and 128 are sealed.

In another alternative representative embodiment (see FIGS. 29A/B), the wet chamber 14 includes a single packaging port 130. In use (see FIG. 29A), the port 130 is coupled to a source 132 of the reconstituting liquid 18 and a vacuum source 134 through a two way valve 136.

Figure 29A:
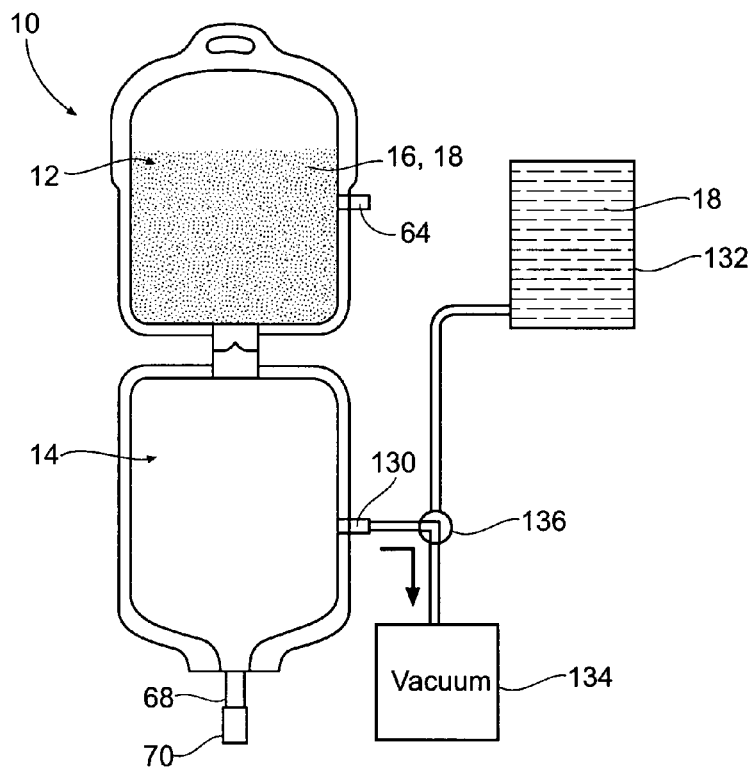
FIGS. 29A and 29B are largely schematic views of another alternative way of packaging the reconstituting liquid for the freeze-dried material in the second chamber of the device of the type shown in FIG. 1 or 22.
Figure 29B:
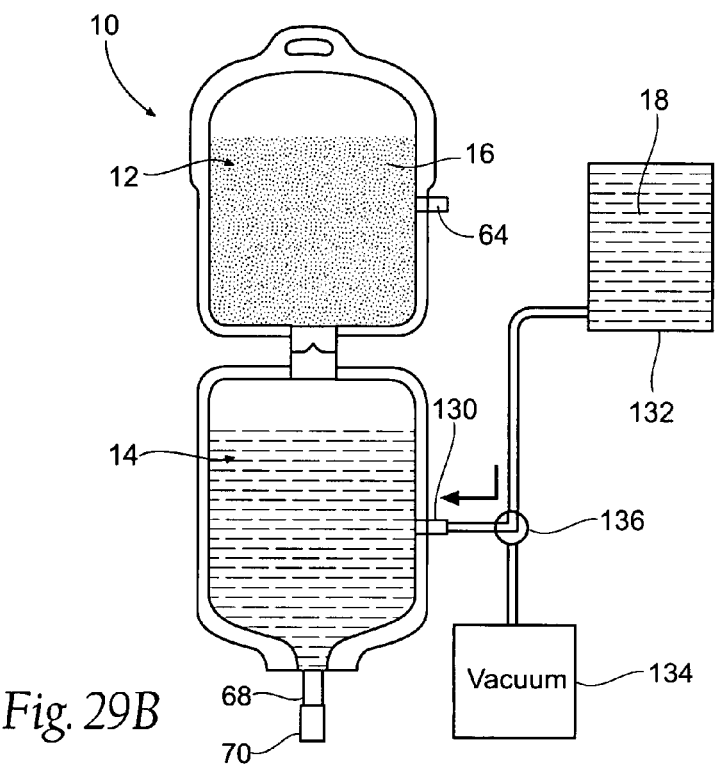

As shown FIG. 29A, the two way valve 136 is operated to close communication with the liquid source 132 and to open communication with the vacuum source 134. A vacuum is applied to the interior of the chamber 14. As shown in FIG. 29B, the two way valve 136 is operated to open communication with the liquid source 132 and to close communication with the vacuum source 134. The reconstituting liquid 18 is conveyed by gravity flow into the chamber 14. The packaging port 130 is sealed.

In both arrangements, the administration port 68 can be inserted and sealed close in a pre-packing operation.

The administration port 68 is not used until it is time to administer the reconstituted freeze-dried material, as shown in FIG. 16.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. Apparatus comprising:
a dry freeze-dried material,
a reconstituting liquid for the freeze-dried material, and
a flexible container including first chamber sized and configured to hold the freeze-dried material in a dry state, a second chamber sized and configured to hold the reconstituting liquid in a wet state, a sealing wall within the flexible container sized and configured to form a barrier between the first chamber and the second chamber preventing contact between the freeze-dried material and the reconstituting liquid, and at least one valve assembly in the sealing wall operative to open a region of the sealing wall to establish fluid flow communication between the first and second chambers,
wherein the valve assembly includes a normally closed septum operative in a normally closed condition maintaining closure between the first and second chambers and an opened condition establishing fluid flow communication between the first and second chambers in response to at least a partially tearing of the septum,
wherein the septum includes a tear member coupled to a pulling member to at least partially tear the septum.

2. Apparatus according to claim 1
further including an outer skirt overlaying an exterior wall of the container in a region of the sealing wall.

3. Apparatus according to claim 2
wherein the outer skirt includes a tear member coupled to a pulling member to tear the outer skirt for removal.

4. Apparatus according to claim 2
wherein the flexible container includes an integral administration port for administering material from the container.

5. Apparatus according to claim 1
wherein the freeze-dried material includes freeze-dried human plasma.

6. Apparatus comprising:
a dry freeze-dried material,
a reconstituting liquid for the freeze-dried material, and
a flexible container including first chamber sized and configured to hold the freeze-dried material in a dry state, a second chamber sized and configured to hold the reconstituting liquid in a wet state, a sealing wall within the flexible container sized and configured to form a barrier between the first chamber and the second chamber preventing contact between the freeze-dried material and the reconstituting liquid, and at least one valve assembly in the sealing wall operative to open a region of the sealing wall to establish fluid flow communication between the first and second chambers,
wherein the valve assembly includes a normally closed septum operative in a normally closed condition maintaining closure between the first and second chambers and an opened condition establishing fluid flow communication between the first and second chambers in response to at least a partially tearing of the septum, wherein the valve assembly includes a pressure sensitive valve operative between a normally closed condition normally resisting fluid flow communication between the first and second chambers and an opened condition establishing fluid flow condition communication between the first and second chambers in response to a pressure differential applied across the valve, and a normally closed septum associated with the valve operative in a normally closed condition maintaining closure between the first and second chambers independent of the valve and an opened condition establishing fluid flow communication between the first and second chambers in response to at least a partially tearing of the septum and a pressure differential applied across the valve.

7. Apparatus according to claim 6 wherein the pressure sensitive valve comprises a flap valve.

8. Apparatus according to claim 6 wherein the septum includes a tear member coupled to a pulling member to at least partially tear the septum.

9. Apparatus comprising:

a dry freeze-dried material, a reconstituting liquid for the freeze-dried material, and a flexible container including first chamber sized and configured to hold the freeze-dried material in a dry state, a second chamber sized and configured to hold the reconstituting liquid in a wet state, a sealing wall within the flexible container sized and configured to form a barrier between the first chamber and the second chamber preventing contact between the freeze-dried material and the reconstituting liquid, and at least one valve assembly in the sealing wall operative to open a region of the sealing wall to establish fluid flow communication between the first and second chambers, wherein the valve assembly includes a normally closed septum operative in a normally closed condition maintaining closure between the first and second chambers and an opened condition establishing fluid flow communication between the first and second chambers in response to at least a partially tearing of the septum, further including an outer skirt overlaying an exterior wall of the container in a region of the sealing wall, wherein at least a portion of the exterior wall of the container overlaid by the outer skirt includes placations.

* * * * *

UNITED STATES PATENT AND TRADEMARK OFFICE
CERTIFICATE OF CORRECTION

PATENT NO. : 7,776,022 B2  Page 1 of 1
APPLICATION NO. : 11/725352
DATED : August 17, 2010
INVENTOR(S) : Simon J. McCarthy, John W. Morgan and William D. Block It is certified that error appears in the above-identified patent and that said Letters Patent is hereby corrected as shown below:

Title Page, Item (73) Assignee: After "Technologies," insert --Inc.-- to correctly read --HemCon Medical Techologies, Inc.--

Signed and Sealed this

Thirtieth Day of November, 2010

David J. Kappos
*Director of the United States Patent and Trademark Office*